(12) United States Patent
Michniewicz et al.

(10) Patent No.: US 10,527,557 B2
(45) Date of Patent: Jan. 7, 2020

(54) ADAPTIVE DIFFUSE ILLUMINATION SYSTEMS AND METHODS

(71) Applicant: Radiant Vision Systems, LLC, Redmond, WA (US)

(72) Inventors: Mark Michniewicz, Holly, MI (US); Andrew Blowers, Carnation, WA (US)

(73) Assignee: Radiant Vision Systems, LLC, Redmond, WA (US)

( * ) Notice: Subject to any disclaimer, the term of this patent is extended or adjusted under 35 U.S.C. 154(b) by 0 days.

(21) Appl. No.: 16/208,028

(22) Filed: Dec. 3, 2018

(65) Prior Publication Data

US 2019/0204236 A1   Jul. 4, 2019

Related U.S. Application Data

(60) Provisional application No. 62/613,852, filed on Jan. 5, 2018, provisional application No. 62/611,718, filed on Dec. 29, 2017.

(51) Int. Cl.
| | |
|---|---|
| *F21V 9/40* | (2018.01) |
| *G01N 21/88* | (2006.01) |
| *F21V 3/02* | (2006.01) |

(52) U.S. Cl.
CPC ........... *G01N 21/8806* (2013.01); *F21V 3/02* (2013.01); *F21V 9/40* (2018.02); *G01N 2021/8825* (2013.01)

(58) Field of Classification Search
CPC .......... G01N 21/8806; F21V 9/40; F21V 3/02

USPC ..................................................... 356/237.2
See application file for complete search history.

(56) References Cited

U.S. PATENT DOCUMENTS

| | | | | |
|---|---|---|---|---|
| 3,439,178 | A * | 4/1969 | Rottmann | B07C 5/126 250/222.1 |
| 4,664,525 | A * | 5/1987 | Tagaya | G01N 21/9054 209/526 |
| 5,175,428 | A * | 12/1992 | Agerskov | B07C 5/3408 250/223 B |
| 7,792,419 | B2 * | 9/2010 | Dunn | G01N 21/8806 396/4 |
| 2007/0097686 | A1 * | 5/2007 | Dunn | G01N 21/8806 362/249.16 |

* cited by examiner

*Primary Examiner* — Roy M Punnoose
(74) *Attorney, Agent, or Firm* — Perkins Coie LLP

(57) ABSTRACT

Systems and methods for illuminating and/or inspecting one or more features of a unit under test (UUT) are disclosed herein. A system configured in accordance with embodiments of the present technology can include, for example, a machine, one or more diffuser elements, and/or one or more light sources. The system can create and adjust brightfield illumination profiles on portions of the UUT by, for example, using the one or more light sources and/or the one or more diffuser elements to adjust diffuse and/or specular illumination projected onto the curved features of the UUT. In some embodiments, the system includes one or more darkfield light sources configured to project illumination onto second portions of the UUT to create a darkfield illumination profile. The system can capture data of the brightfield and/or darkfield illumination profiles and can thereby inspect portions of the UUT.

20 Claims, 15 Drawing Sheets

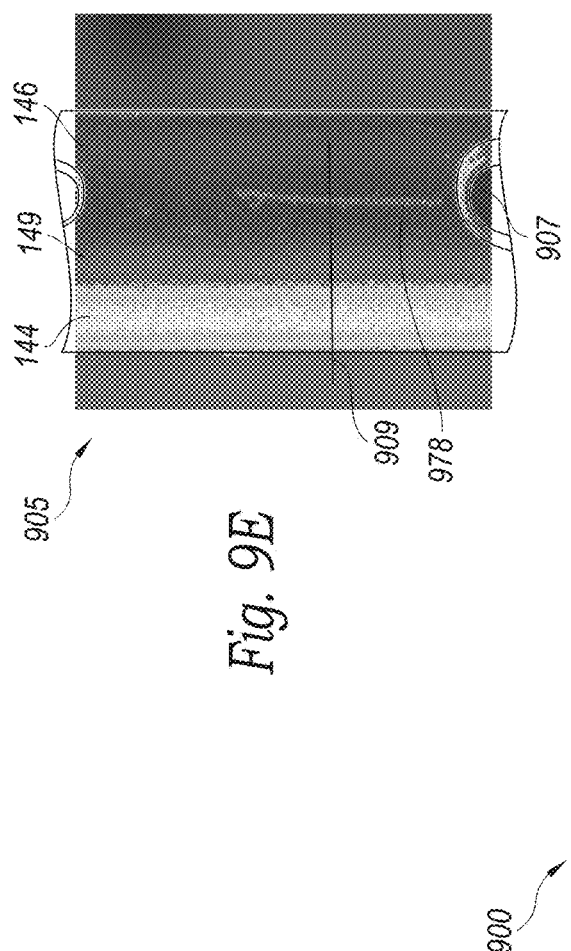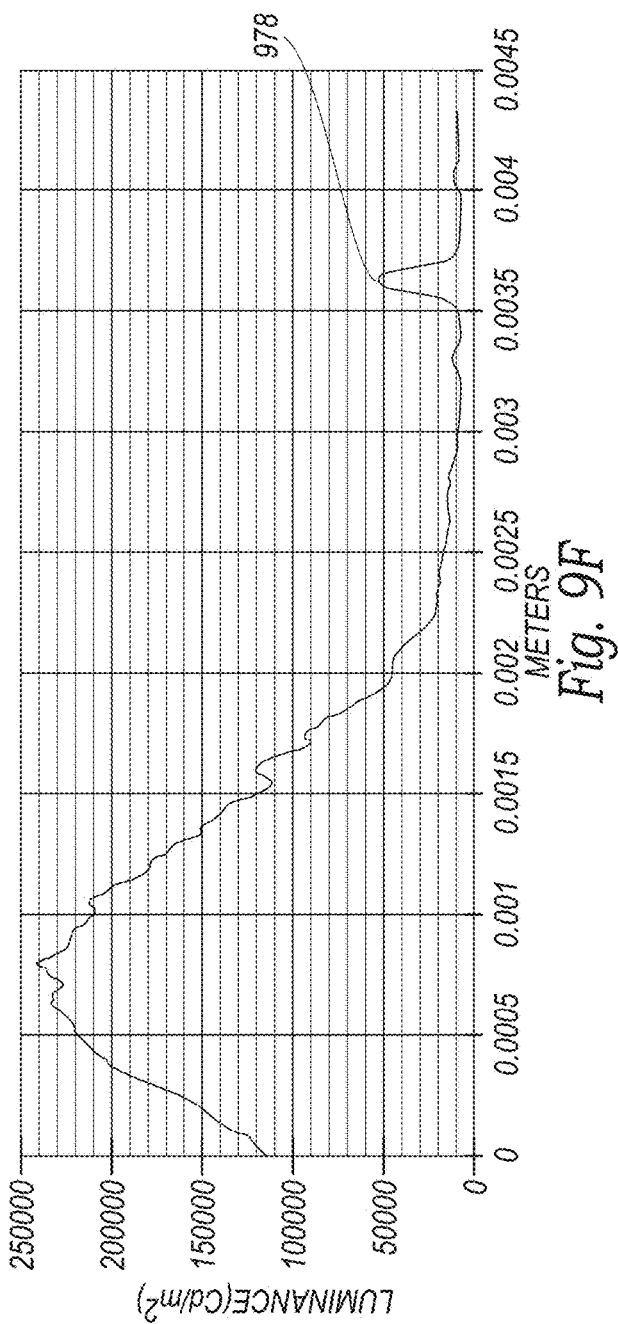
Fig. 9E
Fig. 9F

US 10,527,557 B2

ADAPTIVE DIFFUSE ILLUMINATION SYSTEMS AND METHODS

CROSS-REFERENCE TO RELATED APPLICATION(S)

The present application claims priority to U.S. Provisional Patent Application No. 62/611,718 filed Dec. 29, 2017, and U.S. Provisional Patent Application No. 62/613,852 filed Jan. 5, 2018, the disclosures of which are both incorporated by reference in their entireties.

TECHNICAL FIELD

The present disclosure relates generally to illumination systems for machine vision and, more particularly, to systems having adaptive diffuse illumination capabilities and associated methods.

BACKGROUND

Machine vision is often used in industry in addition to or in lieu of human vision for a variety of applications. One such application is product inspection. During product inspection, a light source uses one or more lighting techniques to illuminate features of a unit under test (UUT) while a camera captures images of those features. Signal processing hardware and software are then used to analyze these images and to identify defects (e.g., cosmetic defects) on the UUT.

A common lighting technique for machine vision is brightfield illumination. Under brightfield illumination, light is directed at a UUT and is reflected back toward a lens of a camera. Software then analyzes abnormal characteristics (e.g., dark spots illustrating attenuation in the light reflected at the camera lens) in images of the UUT taken by the camera to identify, for example, defects in the UUT. However, using brightfield illumination to highlight curved features of a UUT poses several challenges. For example, typical brightfield sources often leave hotspots or saturated areas where the illumination and part geometry of the UUT interact on curved features to reflect more light to the camera from some regions and less from others. This becomes especially prevalent as the surface finish of the curved features becomes more specular than diffuse.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 9E is a luminescence heat map of an illumination profile of a curved surface of an edge feature of a unit under test using the adaptive diffuse illumination system of FIG. 9A.

FIG. 9F is a line plot of luminescence measures along a portion of the illumination profile illustrated in FIG. 9E.

DETAILED DESCRIPTION

A. Overview

Figure 1:
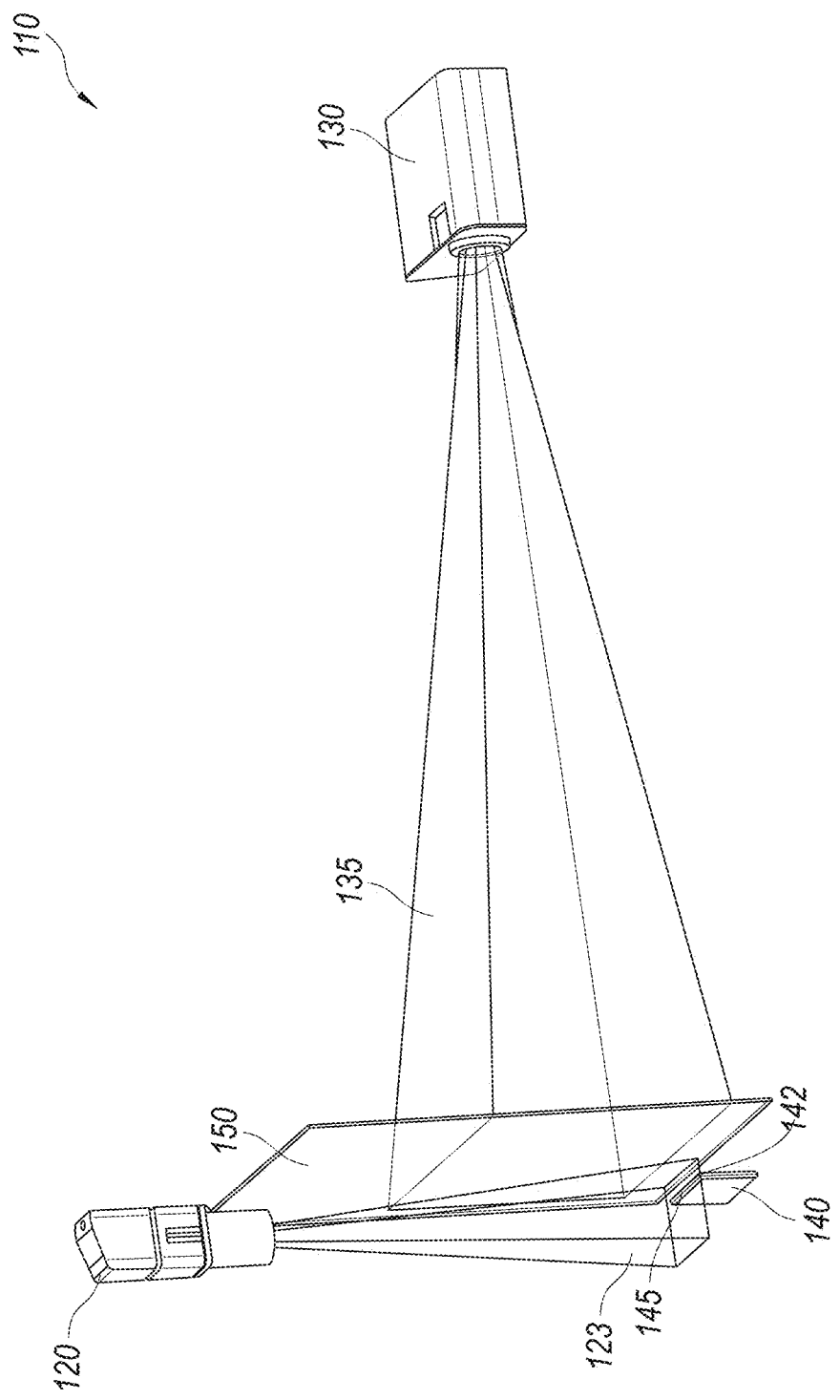
FIG. 1 is an orthogonal view of an adaptive diffuse illumination system configured in accordance with an embodiment of the present technology.

The following disclosure describes adaptive diffuse illumination systems and associated methods for illuminating one or more features of a unit under test (UUT) (e.g., for machine vision). As described in greater detail below, methods and/or systems configured in accordance with embodiments of the present technology are configured to illuminate curved features of a UUT using specular and/or diffuse illumination.

Some embodiments of the present technology use a light source and a diffuser component to illuminate (e.g., uniformly) one or more features of a UUT. In particular, the light source can project specular illumination onto the diffuser component to create diffuse illumination, which is then directed (e.g., focused, reflected, and/or redirected) at the feature(s) of the UUT. A machine (e.g., a camera) captures data of the feature(s) of the UUT. More specifically, the machine captures images of the feature(s) of the UUT (e.g., for concurrent and/or later analysis).

The inventors have recognized that when features of a UUT are curved, specular illumination sources leave hotspots or saturated areas where the brightfield illumination and feature geometry interact to reflect more light to the machine from some regions of the features and less from others. They note that this phenomenon becomes more prevalent when the surface finish of the features become more specular than diffuse. Machine vision analysis and/or inspection in these saturated regions (e.g., for cosmetic defects) is extremely difficult, if not impossible, even with the aid of advanced signal processing techniques. Furthermore, the inventors have also recognized a severe gradient in luminescence measures across illumination profiles of illuminated features (e.g., curved features) of the UUT. In other words, the inventors have recognized that these illumination profiles use a large amount of machine imaging bit depth, meaning there is a low signal to noise ratio in the illumination profile. As a result, accurate and efficient signal processing becomes more difficult to achieve, especially with the increased need for and importance of subsequent signal processing analysis in these scenarios.

Accordingly, embodiments of the present technology use adaptive diffuse illumination techniques to lessen the effects and harsh qualities of specular illumination on features (e.g., curved features) of a UUT. In some embodiments, for example, the present technology uses diffuse, brightfield illumination to create an illumination profile of a feature of the UUT that is (1) more uniform across (e.g., a width of) the feature and/or (2) further below a saturation level of the machine than illumination profiles created using specular illumination alone. The present technology can then adjust the illumination profile (e.g., during exposure to the machine) to make the illumination profile more uniform and/or even further below the saturation level of the machine by, for example, adjusting (e.g., shaping, coloring, patterning, filtering, changing the intensity of) the specular and/or diffuse illumination projected onto the feature of the UUT.

In contrast to the present technology, conventional systems for illuminating curved features of a UUT typically include dome-style cloudy day illuminator systems. Dome-style illuminator systems, however, can become large or unwieldy (especially when a UUT has long linear radius features), and can limit the versatility of these systems to inspect an assortment of UUTs having a range of sizes. In addition, these systems are not amenable to illumination of radial surfaces on the edge of larger, flat UUTs; and they do not provide great flexibility with regard to an array of possible UUT positions. Furthermore, much of the illumination projected from light sources within dome-style illuminator systems goes unused during inspection. Moreover, these systems are often prone to ghosting and/or attenuation in imaging of a UUT (e.g., due to the requirement of a beam splitter for on-axis illumination and imaging). Other conventional systems include phase shifting deflectometry systems. These systems, when applied to relatively long or large parts, often exhibit gross keystone distortions when using area array cameras.

Additionally or alternatively, these and other conventional systems often apply a gradient offset or image compensation during subsequent signal processing of captured images. This technique includes subtracting gray level from non-uniform areas of an illumination profile of a feature of a UUT. To apply this technique effectively, however, the image must not be saturated. Thus, this may be an undesirable solution on its own because it can severely limit useable inspection image bit depth.

In contrast with these conventional systems, embodiments of the present technology have reasonably-sized and/or scalable parts; allow on-axis imaging with little to no ghosting, attenuation, or gross keystone distortion with most or all machine types; use a larger percentage of projected illumination; provide a broad range of possible UUT positions and/or orientations; and/or provide easy access to the UUT. Furthermore, embodiments of the present technology are expected to create and/or adjust illumination profiles on one or more features (e.g., one or more curved features) of a UUT that are relatively uniform and well below the saturated level of most machines (e.g., cameras). As a result, the present technology is expected to (1) minimize and/or eliminate the need for and/or importance of downstream image processing techniques and/or corrections, and/or (2) decrease the amount of time required to adequately and/or accurately analyze (e.g., inspect) features (e.g., curved features) of a UUT.

Furthermore, embodiments of the present technology can include darkfield illumination capabilities in addition to, or in lieu of, the above described brightfield illumination capabilities. Darkfield illumination capability allows embodiments of the present technology to analyze one or more features of a UUT that are not currently and/or cannot be illuminated and/or analyzed with brightfield illumination techniques. Thus, darkfield illumination capability is expected to (1) increase the flexibility and/or versatility of systems in accordance with these embodiments, (2) decrease the amount of time required to adequately and/or accurately analyze features of a UUT, and/or (3) minimize and/or eliminate the need for and/or importance of downstream image processing techniques and/or corrections.

Certain details are set forth in the following description and in FIGS. 1-10 to provide a thorough understanding of various embodiments of the disclosure. However, other details describing well-known structures and systems often associated with illumination and/or machine vision systems and associated methods are not set forth below to avoid unnecessarily obscuring the description of various embodiments of the disclosure.

Many of the details, dimensions, angles, and other features shown in FIGS. 1-10 are merely illustrative of particular embodiments of the disclosure. Accordingly, other embodiments can have other details, dimensions, angles, and features without departing from the spirit or scope of the present disclosure. In addition, those of ordinary skill in the art will appreciate that further embodiments of the disclosure can be practiced without several of the details described below.

B. Embodiments of Adaptive Diffuse Illumination Systems and Associated Methods

FIG. 1 and the following discussion provide a brief, general description of a suitable environment in which a system for illuminating and/or analyzing one or more features of a unit under test (UUT) may be implemented. Although not required, some aspects of the invention are described in the general context of computer-executable instructions, such as routines executed by a general-purpose computer, a personal computer, a server, or other computing system. The invention can also be embodied, at least in part, in a special-purpose computer or data processor that is specifically programmed, configured, or constructed to perform one or more of the computer-executable instructions explained in detail herein. Indeed, the terms "computer" and "computing device," as used generally herein, refer to devices that have a processor and non-transitory memory, as well as any data processor or any device capable of communicating with a network. Data processors include programmable general-purpose or special-purpose microprocessors, programmable controllers, application-specific integrated circuits (ASICs), programming logic devices (PLDs), or the like, or a combination of such devices. Computer-executable instructions may be stored in memory, such as random-access memory (RAM), read-only memory (ROM), flash memory, or the like, or a combination of such components. Computer-executable instructions may also be stored in one or more storage devices such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

FIG. 1 is an orthogonal view of an adaptive diffuse illumination system 110 configured in accordance with an embodiment of the present technology. As shown, the system 110 includes a light source 130, a diffuser screen 150, and a machine 120. Although not shown so as to avoid unnecessarily obscuring the description of the embodiment of the technology, the system 110 can also include other hardware and/or components necessary for machine vision, including one or more processors, software, and/or output devices. For example, the system 110 can include signal processing hardware and/or software to analyze data captured by the machine 120, and/or a display for providing feedback (e.g., that a defect has been detected, that no defects were identified, that any identified defects are within a tolerance threshold, etc.) to a system user.

In operation, the system 110 is configured to visually inspect one or more features of a unit under test 140 ("UUT 140") (e.g., for defects and/or other characteristics). In FIG. 1, the UUT 140 is a mobile device having an edge feature 142 with a curved surface 145. In other embodiments, however, the UUT 140 can be any other object and/or device that can be subjected to machine vision and/or inspection. For example, the UUT 140 in other embodiments can be any object and/or device that has a specular surface with a principle axis of curvature significantly longer than the subsequent radii of additional axes (e.g., an appliance part, a vehicle part and/or trim, durable good surfaces, an edge of a laptop cover, etc.). In some embodiments, the system 110 can include clamps and/or stands (not shown) to position and/or orient one or more features of the UUT 140 toward the machine 120. As described in greater detail below, the system 110 overcomes several challenges of uniformly illuminating one or more curved features of a UUT (e.g., curved surface 145 of edge feature 142 of UUT 140). Even so, the system 110 is not limited to uniformly illuminating curved feature(s) of a UUT, and a person skilled in the art will readily recognize that the system 110 can be used to illuminate (e.g., uniformly or otherwise) other features of a UUT having various shapes, contours, and/or characteristics.

In accordance with embodiments of the present technology, the light source 130 of the system 110 can be any source of illumination configured to project illumination (e.g., in the direction of the UUT 140). For example, the light source 130 can be a light bar, a light bulb, a lamp, a flashlight, a laser, a light emitting diode (LED), an array of LEDs, a flat panel display, and/or another type of light source. In the embodiment illustrated in FIG. 1, the light source 130 is a projector configured to focus specular illumination 135 toward the diffuser screen 150 and/or the UUT 140. As described in greater detail below, the light source 130 of FIG. 1 can be configured to project various illumination intensities, patterns, shapes, and/or colors toward the UUT 140. In this manner, the system 110 can create and/or adjust an illumination profile of one or more features of the UUT 140 (e.g., of the curved surface 145 of the edge feature 142).

The diffuser screen 150 of FIG. 1 is a flat projection screen sized according to the radius length of an inspected feature (e.g., of edge feature 142) of the UUT 140 and to a field of view 123 of the machine 120. More specifically, the size of the diffuser screen 150 is determined according to the ray propagation of the illumination from the point of observation of the machine 120. In operation, the diffuser screen 150 is configured to lessen and/or remove directional properties of an intensity pattern of specular illumination 135 projected onto the diffuser screen 150 by the light source 130. In particular, the diffuser screen 150 of system 110 is configured to shape, spread, and/or disperse focused, specular illumination 135 incident on the diffuser screen 150 into diffuse illumination. In this manner, the diffuser screen 150 increases the apparent beam size of the specular illumination 135 (thereby minimizing and/or eliminating unwanted shadows in an illumination profile of the UUT 140) while also decreasing the illumination intensity of the specular illumination 135 (thereby minimizing and/or eliminating hotspots and/or saturated areas). Thus, the diffuser screen 150 alters the illumination profile of the UUT from the perspective of the machine 120 and minimizes and/or eliminates the need for and/or importance of imaging processing intensity corrections.

Although the system 110 illustrated in FIG. 1 includes a diffuser screen 150, adaptive diffuse illumination systems configured in accordance with other embodiments of the present technology can include other types of diffuser components. For example, some embodiments may utilize a diffuser panel (e.g., a wall or other flat object). In these and other embodiments, diffuser component(s) can be curved and/or arced as described in greater detail below. Furthermore, although the diffuser screen 150 illustrated in FIG. 1 is translucent such that illumination can pass through it, diffuser component(s) in other adaptive diffuse illumination systems can be opaque and configured to reflect illumination at the UUT 140. In still further embodiments, the diffuser component(s) can be transparent. Moreover, although shown separate from the light source 130 in the embodiment illustrated in FIG. 1, in other embodiments the diffuser screen 150 can incorporate and/or can be attached to the light source 130. For example, in some embodiments, the diffuser screen 150 can be placed (e.g., as a cap) over a lens of the light source 130. In these and other embodiments, the diffuser screen 150 can be patterned to alter at least a portion of the specular illumination 135 projected from the light source 130 and/or before the specular illumination 135 reaches the UUT 140. For example, the diffuser screen 150 can be passive and can be manufactured with a specific pattern and/or can have a pattern subsequently applied (e.g., affixed) to it. Additionally or alternatively, the diffuser screen 150 can be active, and can be programmed or otherwise configured to project and/or exhibit a specific pattern (e.g., before the UUT 140 is illuminated and/or in response to feedback regarding a previous and/or current illumination profile). In these and still other embodiments, the diffuser screen 150 can include openings in the screen to permit at least a portion of the specular illumination 135 from the light source 130 to pass through the diffuser screen 150 unhindered on its way to the UUT 140. In still further embodiments, the system 100 may not include the diffuser screen 150.

In the embodiment illustrated in FIG. 1, the machine 120 is a camera (e.g., a digital and/or analog camera) configured for machine vision. For example, the machine 120 can be an area scan camera configured to take interlaced and/or progressive scans of one of more features of the UUT 140. In these and other embodiments, the machine 120 can be a line scan camera (e.g., a conventional line scan camera or a time delay and integration (TDI) camera). In these and still other embodiments, the machine 120 can have two-dimensional and/or three-dimensional imaging capabilities. As noted above, the machine 120, in some embodiments, can include and/or can be operably coupled to other hardware, software, and/or output devices. For example, the machine 120 can be coupled to a computer (not shown) that includes signal processing hardware and/or software to analyze data captured by the machine 120. Additionally or alternatively, the machine 120 can be coupled to one or more displays configured to provide feedback to a system user. In these and other embodiments, the machine 120 can include onboard signal processing hardware and/or software and/or can include an onboard display. Furthermore, although the system 110 is shown with a single machine 120 in FIG. 1, the system 110 can include more than one machine (e.g., machine 120) in other embodiments (e.g., to inspect the same and/or one or more other features of the UUT 140).

In the embodiment illustrated in FIG. 1, the light source 130 of system 110 is positioned perpendicular to the UUT 140 and is configured to project specular illumination 135 toward the diffuser screen 150. The diffuser screen 150 is positioned (a) between the light source 130 and the UUT 140, (b) parallel to the UUT 140 and the machine 120, and (c) just outside a field of view 123 ("FOV 123") (e.g., an orthogonal field of view) of the machine 120. This system orientation allows broad access to the UUT and/or a broad range of possible UUT positions and/or orientations. Furthermore, this orientation allows for a manageable system size and permits the FOV 123 of the machine 120 to remain orthogonal to the curved surface 145 of the UUT 140. In addition, this system orientation permits on-axis illumination and data capture with little to no ghosting, attenuation, or gross keystone distortions that are noticeable in conventional machine vision illumination systems and techniques.

In operation, the system 110 of FIG. 1 is configured to uniformly illuminate the curved surface 145 of the edge feature 142 of the UUT 140. During illumination, the machine 120 captures data (e.g., analog and/or digital images) of a portion (e.g., all or a subset) of the curved surface 145 within its field of view 123 ("FOV 123"). Data captured by the machine 120 can then be passed to signal processing hardware and/or software to identify defects on the curved surface 145 of the edge feature 142 of the UUT 140. For example, data captured by the machine 120 can be analyzed to identify defects (e.g., cosmetic defects) and/or to distinguish defects from proper components and/or desired characteristics of the curved surface 145 of the edge feature 142 of the UUT 140. Shaping the intensity of illumination incident on the diffuser screen 150 minimizes and/or eliminates saturated areas from an illumination profile of an illuminated feature of the UUT. As a result, the system 110 minimizes the need for and/or importance of imaging processing intensity corrections (e.g., of applying a gradient offset or image compensation to the data by subtracting gray level from non-uniform areas). Furthermore, the efficacy and/or efficiency of signal processing analysis and techniques are increased.

Figure 2:
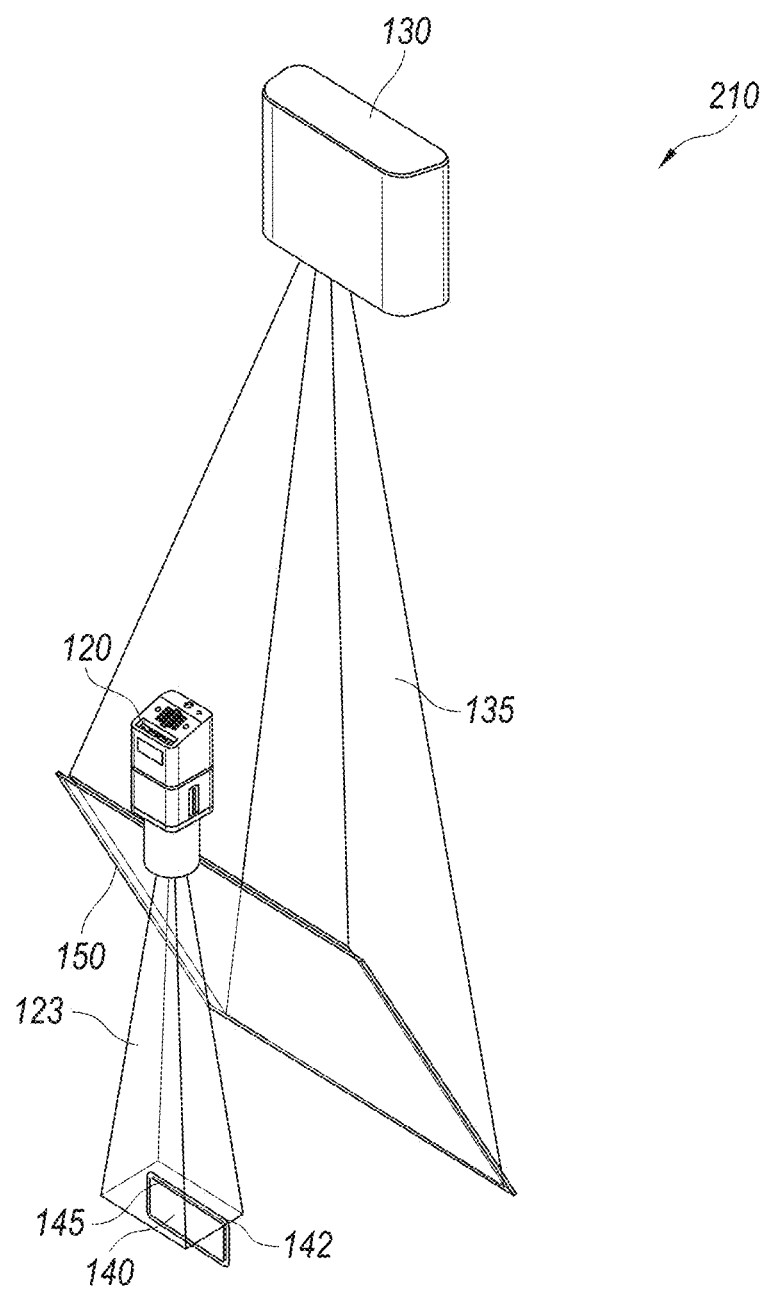
FIG. 2 is an isometric view of an adaptive diffuse illumination system configured in accordance with another embodiment of the present technology.

Although the system 110 is shown in FIG. 1 with a diffuser screen 150 aligned parallel with the UUT 140 and with a light source 130 aligned perpendicular to the UUT 140, other adaptive diffuse illumination systems in accordance with other embodiments can utilize a diffuser screen 150 and/or a light source 130 at a variety of positions, angles, and/or orientations (e.g., dependent on one or more characteristics and/or features of the UUT 140). For example, FIG. 2 illustrates a system 210 in accordance with another embodiment of the present technology. As shown, the diffuser screen 150 is aligned at a 45-degree angle with respect to the UUT 140. Furthermore, the light source 130 is positioned above the machine 120 and is similarly aligned at a 45-degree angle with respect to the UUT 140. In other embodiments, the light source 130 can be aligned at a different angle with respect to the UUT 140 than the angle in which the diffuser screen 150 is aligned with respect to the UUT 140.

In still other embodiments, an adaptive diffuse illumination system can include different diffuser screen and/or light source positions and/or orientations. For example, in some embodiments, the light source 130 can be positioned between and/or below the diffuser screen 150 and the UUT 140. In these embodiments, the light source 130 can be configured to project specular illumination 135 at the diffuser screen 150, which, in turn, can reflect diffuse illumination toward one or more features of the UUT 140. In other embodiments, the light source 130 can be configured to project specular illumination 135 at one or more features of the UUT 140, and the diffuser screen 150 can be configured to redirect illumination reflected off of the UUT 140 back toward the UUT 140. In these and still other embodiments, an adaptive diffuse illumination system can include more than one diffuser screen 150 and/or more than one light source 130 at any desired position, angle, and/or orientation. For example, diffuser screen 150 can be positioned to surround the FOV 123 of the machine 120. Furthermore, some of these embodiments can have more than one light source 130 configured to project specular illumination 135 onto the same diffuser screen 150 and/or can have one or more diffuser screens 150 configured to reflect specular and/or diffuse illumination toward the UUT 140. In this manner, the adaptive diffuse illumination systems can create and/or adjust one or more (e.g., customized) illumination profiles (e.g., one or more uniform and/or other illumination profiles) on one or more features of the UUT 140 (e.g., on the curved surface 145 of the edge feature 142).

Figure 3A:
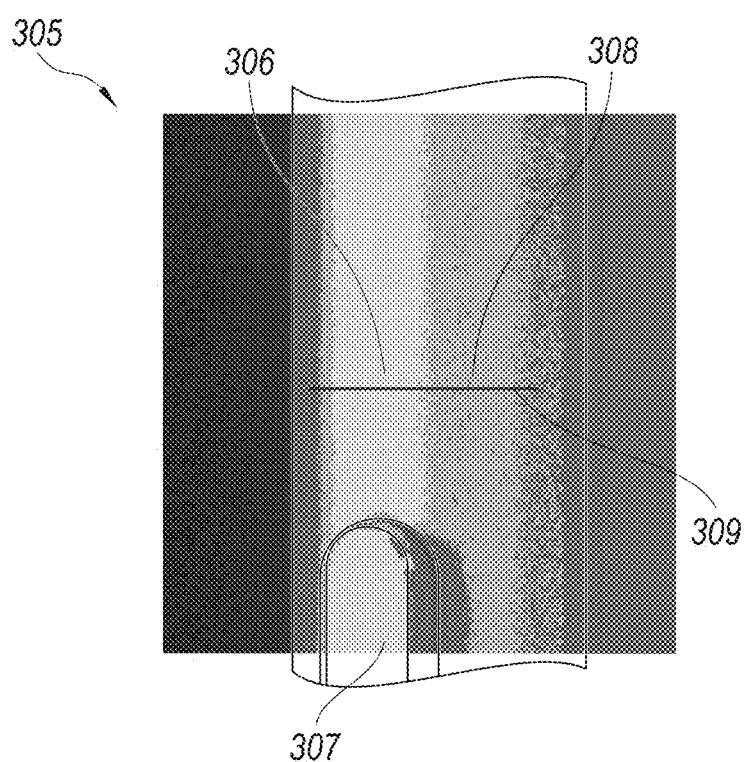
FIG. 3A is a luminescence heat map of an illumination profile of a curved surface of an edge feature of a unit under test using a conventional brightfield illumination system.
Figure 3B:
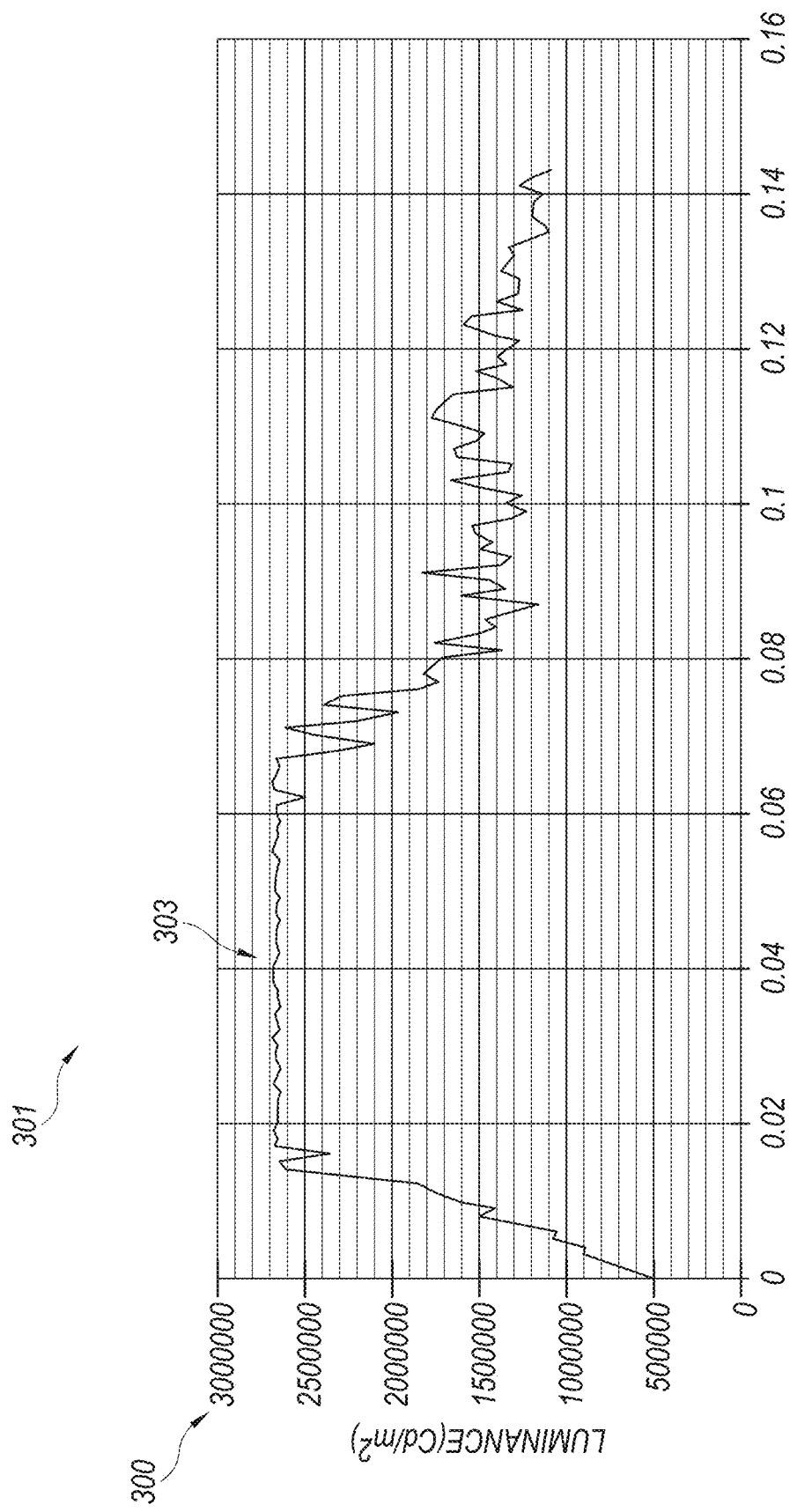
FIG. 3B is a line plot of luminescence measures along a portion of the illumination profile illustrated in FIG. 3A.

FIG. 3A is a luminescence heat map 305 of an illumination profile of a curved surface of an edge feature of a UUT (e.g., the curved surface 145 of the edge feature 142 of the UUT 140 of FIG. 1) created using a conventional brightfield illumination system (e.g., a light bar and a machine without a diffuser screen). FIG. 3B is a line plot 300 of luminescence measures along a portion of the illumination profile illustrated in FIG. 3A. More specifically, the x-axis of the line plot 300 traces a portion 309 of the illumination profile illustrated in FIG. 3A. For purposes of illustration, the portion 309 was intentionally selected to trace the width of the curved surface of the UUT and to exclude a known component 307 of the edge feature of the UUT.

The line plot 300 of FIG. 3B represents a measure of the luminescence along the portion 309 constrained to the imaging capability of the machine (e.g., machine 120; FIG. 1) of the conventional system. Thus, a plateau 303 in luminescence is noticeable in FIG. 3B between 0.02 and 0.06 meters along the portion 309 because luminescence measurements in this region exceed the imaging capability of the machine (e.g., approximately 2,500,000 $Cd/m^2$). This region corresponds to region 306 of the portion 309 in FIG. 3A. True measurements of luminescence in the region 306 (e.g., measurements that are not constrained to the imaging capability of the machine) exceed the plateau 303, and a line plot of the true measurements would illustrate a peak in luminescence at the location generally indicated by arrow 301 in FIG. 3B (e.g., significantly above the plateau 303 in the line plot 300 and summiting between approximately 3,000,000 and 4,000,000 Cd/m$^2$). Thus, the region 306 of the portion 309 corresponds to a saturated region of the illumination profile illustrated in FIG. 3A. Furthermore, when factoring in the peak at the location indicated by arrow 301, a severe gradient of luminescence is noticeable across the entirety of the portion 309. There is also a noticeably severe gradient even across a non-saturated region 308 (FIG. 3A) of the portion 309 (e.g., illustrated from about 0.08 meter to about 0.14 meter in the line plot 300 of FIG. 3B).

As explained above, the large luminescence measures in the region 306 of the portion 309 and the severe gradient of luminescence across the portion 309 result from an interaction between specular illumination from the light bar and part geometry (e.g., the curved surface) of a feature (e.g., the edge feature) of the UUT. Because luminescence measures in the saturated region 306 exceed the imaging capability of the machine, it becomes extremely difficult, if not impossible, to identify defects and/or distinguish defects from known components and/or desired characteristics of the UUT within this region 306 without more expensive and more technologically complex machines and/or systems to capture and/or analyze these luminescence values. It is similarly difficult to identify defects and/or distinguish defects from known components and/or desired characteristics of the UUT even in the non-saturated region 308 with the presence of such a severe gradient of luminescence illustrated in the line plots 300 and 302. As a result, (a) the need for and/or importance of downstream imaging processing techniques and/or corrections, and/or (b) the time required to adequately and/or accurately inspect the feature of the UUT increase.

Figure 4A:
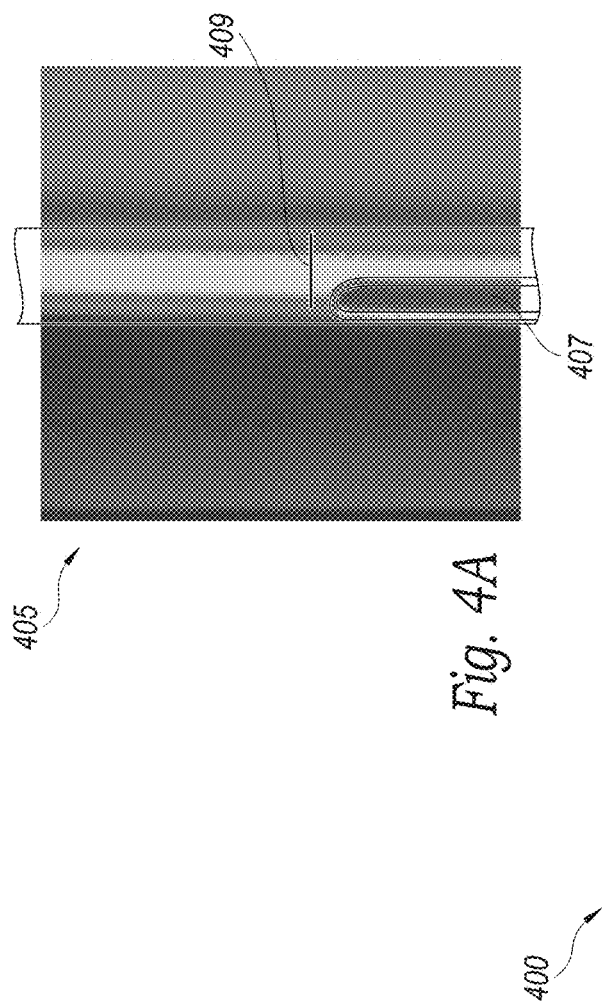
FIG. 4A is a luminescence heat map of an illumination profile of a curved surface of an edge feature of a unit under test using the adaptive diffuse illumination system of FIG. 1.
Figure 4B:
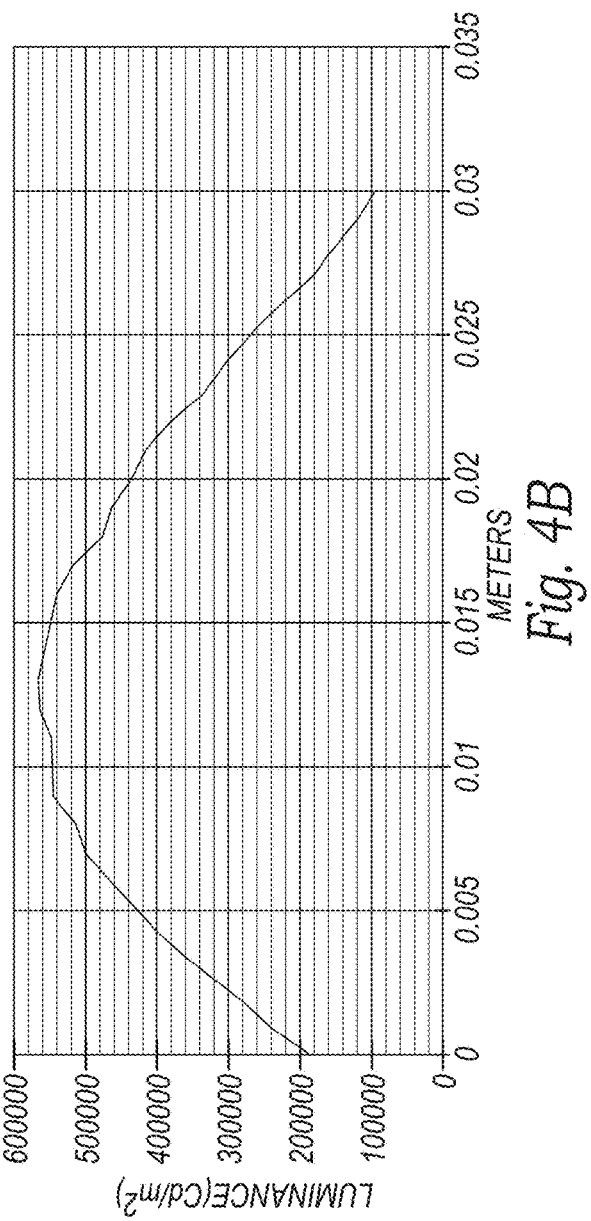
FIG. 4B is a line plot of luminescence measures along a portion of the illumination profile illustrated in FIG. 4A.

In contrast, FIG. 4A is a luminescence heat map 405 of an illumination profile of a curved surface of a UUT (e.g., the curved surface 145 of the edge feature 142 of the UUT 140 of FIG. 1) created using the adaptive diffuse illumination system 110 of FIG. 1. FIG. 4B is a line plot of luminescence measures along a portion of the illumination profile illustrated in FIG. 4A. More specifically, the x-axis of the line plot 400 in FIG. 4B traces a portion 409 of the illumination profile illustrated FIG. 4A. For purposes of illustration, the portion 409 was intentionally selected to trace the width of the curved surface of the UUT and to exclude a known component 407 of the edge feature of the UUT. The line plot 400 of FIG. 4B represents a true measure of luminescence along the portion 409. As shown, luminescence measures across the entirety of the portion 409 are well below the saturation value of the machine (e.g., approximately 2,500,000 Cd/m$^2$, as explained above). Thus, there is not a saturated region in the portion 409, meaning that the adaptive diffuse illumination system 110 can inspect the entire range of the portion 409. Furthermore, and as shown in FIG. 4A, the portion 409 is a representative portion of the majority of the illustrated illumination profile, and the luminescence measures in the portion of the illumination profile that corresponds to the known component 407 are nowhere near the luminescence measures of the region 306 (FIGS. 3A and 3B) or the saturation level of the machine. This means that the system 110 can also inspect the entirety of the illumination profile of the curved surface of the UUT illustrated in FIG. 4A. Moreover, the gradient of illumination across the portion 409 is far less severe than the corresponding gradient of portion 309 illustrated in FIGS. 3A and 3B. Therefore, the system 110 is expected to more easily and/or efficiently identify defects (e.g., cosmetic defects) and/or distinguish defects from known components (e.g., the known component 407) and/or desired characteristics of the UUT. This, in turn, (a) minimizes and/or eliminates the need for and/or importance of downstream imaging processing techniques and/or corrections, and/or (b) decreases the amount of time required to adequately and/or accurately inspect the curved surface of the UUT.

In some embodiments, it may be desirable to color, shape, pattern, and/or otherwise alter illumination projected toward the UUT (e.g., to create and/or adjust an illumination profile and/or to achieve an even greater decrease in luminescence values and/or gradient). As explained above with respect to FIG. 1, the diffuser screen 150 can be configured to color, shape, and/or pattern illumination projected at the UUT 140. For example, the diffuser screen 150 (a) can be active and/or passive to take on a specific pattern, (b) can be a specific color, (c) can be configured to pass one or more specific colors and/or intensities of illumination, (d) can include one or more (e.g., polarization, color, and/or intensity) filters, and/or (e) can include openings to permit illumination to pass unhindered on its way to the UUT 140.

Figure 5A:
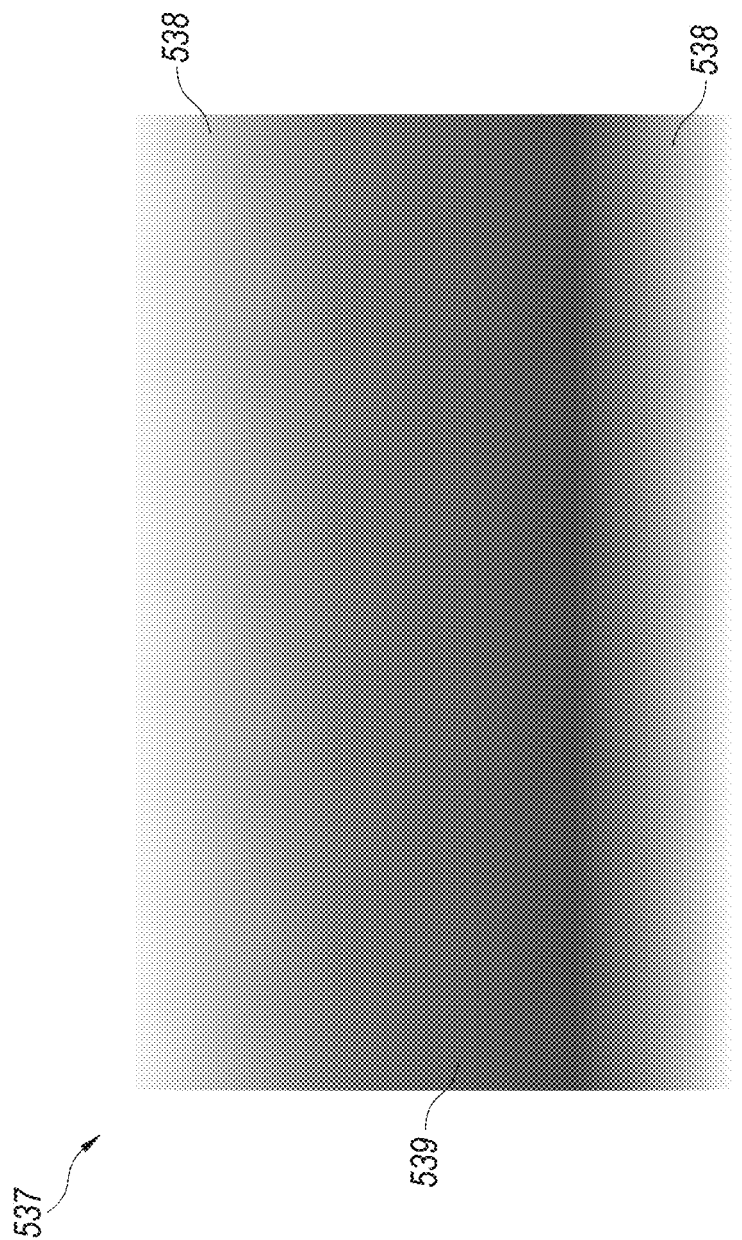
FIG. 5A is a gradient pattern of illumination projected from a light source of an adaptive diffuse illumination system configured in accordance with an embodiment of the present technology.

Additionally or alternatively, the light source 130 can be configured to color, shape, pattern, and/or otherwise alter illumination projected at the UUT 140. For example, the light source 130 in FIG. 1 can be a projector, and the adaptive diffuse illumination system 110 can leverage the various capabilities of the projector light source 130 to create and/or adjust an illumination profile on the UUT 140. To illustrate this point, FIG. 5A is provided to give an example of a gradient pattern of illumination 537 that can be projected from the light source 130 onto the diffuser screen 150. As shown in FIG. 5A, the gradient pattern of illumination 537 includes two high-luminescence regions 538 and a low-luminescence region 539. The high-luminescence regions 538 of the gradient pattern of illumination 537 can, for example, align with dark and/or normal areas exhibited in an illumination profile of the curved surface 145 of the edge feature 142 of the UUT 140. The low-luminescence region 539 can, for example, align with bright spots exhibited in the illumination profile of the curved surface 145 of the UUT 140. In this manner, the adaptive diffuse illumination system 110 can manipulate illumination projected onto the UUT 140 (e.g., with or without using the diffuser screen 150) to create a (e.g., uniform) illumination profile and/or to adjust (e.g., to make uniform) an illumination profile of the UUT 140 (e.g., across all or a portion of the curved surface 145).

In some embodiments, the light source 130 can be configured to automatically adjust the illumination profile (e.g., based on feedback from the machine 120, the signal processing hardware and/or software, and/or other components of the system 110). For example, the system 110 can project an initial pattern of specular illumination (e.g., a dotted or gradient pattern) onto the UUT using the light source 130 and/or the diffuser screen 150 and can observe the resulting illumination profile on the UUT. Various components of the system 110 (e.g., the signal processing hardware and/or software) can then identify, for example, adjustments (e.g., a calibration and/or source map) that can be used to modify the pattern of illumination by adjusting the light source 130 and/or the diffuser screen 150. In this manner, the system 110 can create and/or adjust an illumination profile (e.g., a uniform illumination profile) customized to a feature of the UUT. In these and other embodiments, the light source 130 and/or the diffuser screen 150 can be configured to adjust the illumination profile in response to instructions (e.g., from a user of the system and/or other components of the system 110). In these and still other embodiments, a user can manually adjust, program, and/or otherwise configure the light source 130 and/or the diffuser screen 150 to create and/or adjust the illumination profile.

Figure 5B:
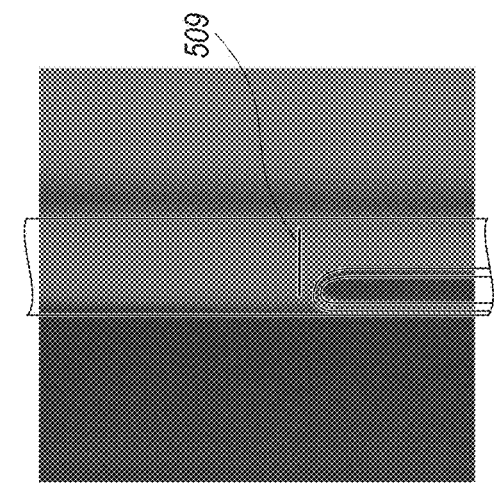
FIG. 5B is a luminescence heat map of an illumination profile of a curved surface of an edge feature of a unit under test using the adaptive diffuse illumination system of FIG. 1 and the gradient pattern of illumination of FIG. 5A.
Figure 5C:
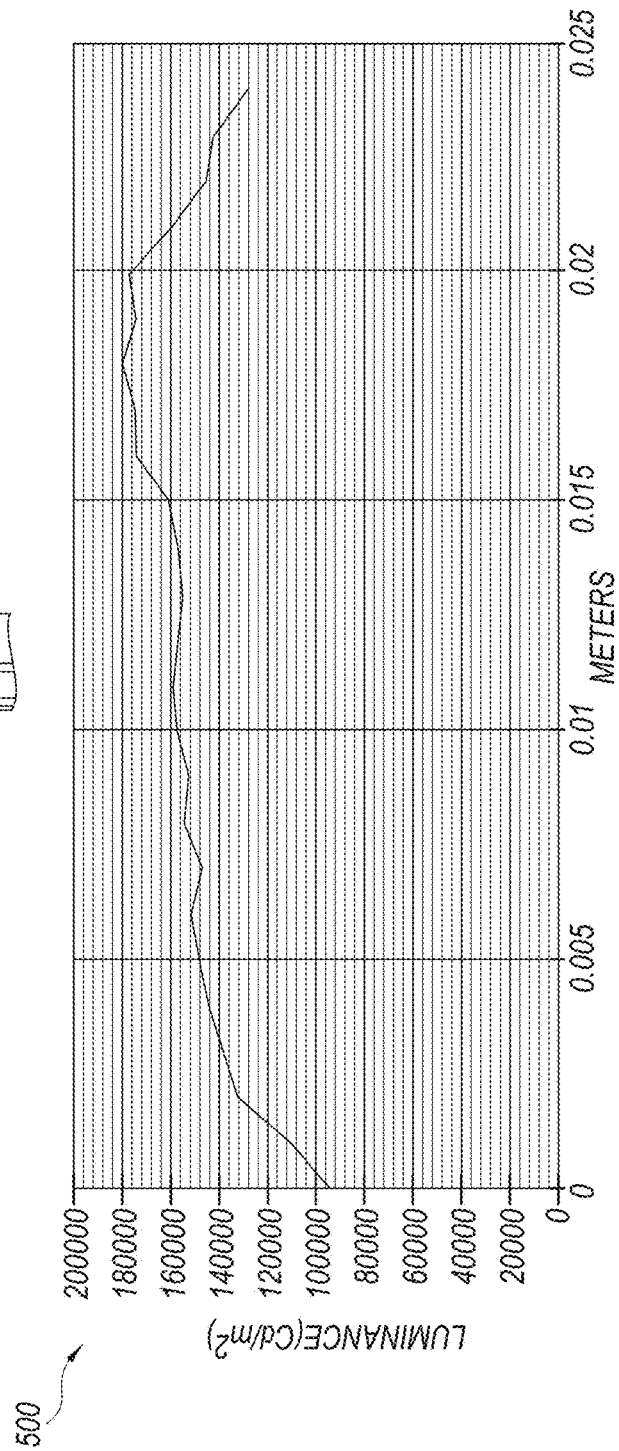
FIG. 5C is a line plot of luminescence measures along a portion of the illumination profile illustrated in FIG. 5B.

FIG. 5B is a luminescence heat map 505 of an illumination profile of a curved surface of a UUT (e.g., curved surface 145 of edge feature 142 of UUT 140 from FIG. 1) created using the adaptive diffuse illumination system 110 of FIG. 1 and the gradient pattern of illumination 537 illustrated in FIG. 5A. FIG. 5C is a line plot 500 of the true measure of luminescence along a portion of the illumination profile illustrated in FIG. 5B. More specifically, the x-axis of the line plot 500 in FIG. 5C traces a portion 509 of the illumination profile illustrated in FIG. 5B. As shown, luminescence measures across the entirety of the portion 509 are even further below the saturation value of the machine (e.g., approximately 2,500,000 $Cd/m^2$, as explained above) than the luminescence measures across the portion 409 illustrated in FIGS. 4A and 4B (e.g., luminescence measures taken with system 110 but without the gradient pattern of illumination 537). Thus, there is similarly not a saturated region in the portion 509 or in the illumination profile illustrated in FIG. 5B. Therefore, the adaptive diffuse illumination system 110 can inspect the entire range of the curved surface of the UUT. Furthermore, the gradient of illumination across the portion 509 is drastically decreased from even the corresponding gradient of the portion 490 illustrated in FIGS. 4A and 4B, let alone from the corresponding gradient of the portion 309 illustrated in FIGS. 3A and 3B. In other words, significantly less camera bit depth is consumed by the illumination intensity profile illustrated in FIG. 5B, meaning that there is a greater signal-to-noise ratio. As a result, the inspection capability of the system 110 is increased because defects (e.g., cosmetic defects) in the curved surface of the UUT are even more prevalent than they were using the system 110 without the gradient pattern of illumination 537 and/or without the diffuser screen 150 and/or can more easily be distinguished from known components and/or desired characteristics of the UUT. Accordingly, (1) the need for and/or importance of downstream imaging processing techniques and/or corrections and/or (2) the amount of time required to adequately and/or accurately inspect the curved surface of the UUT are greatly reduced.

Figure 6A:
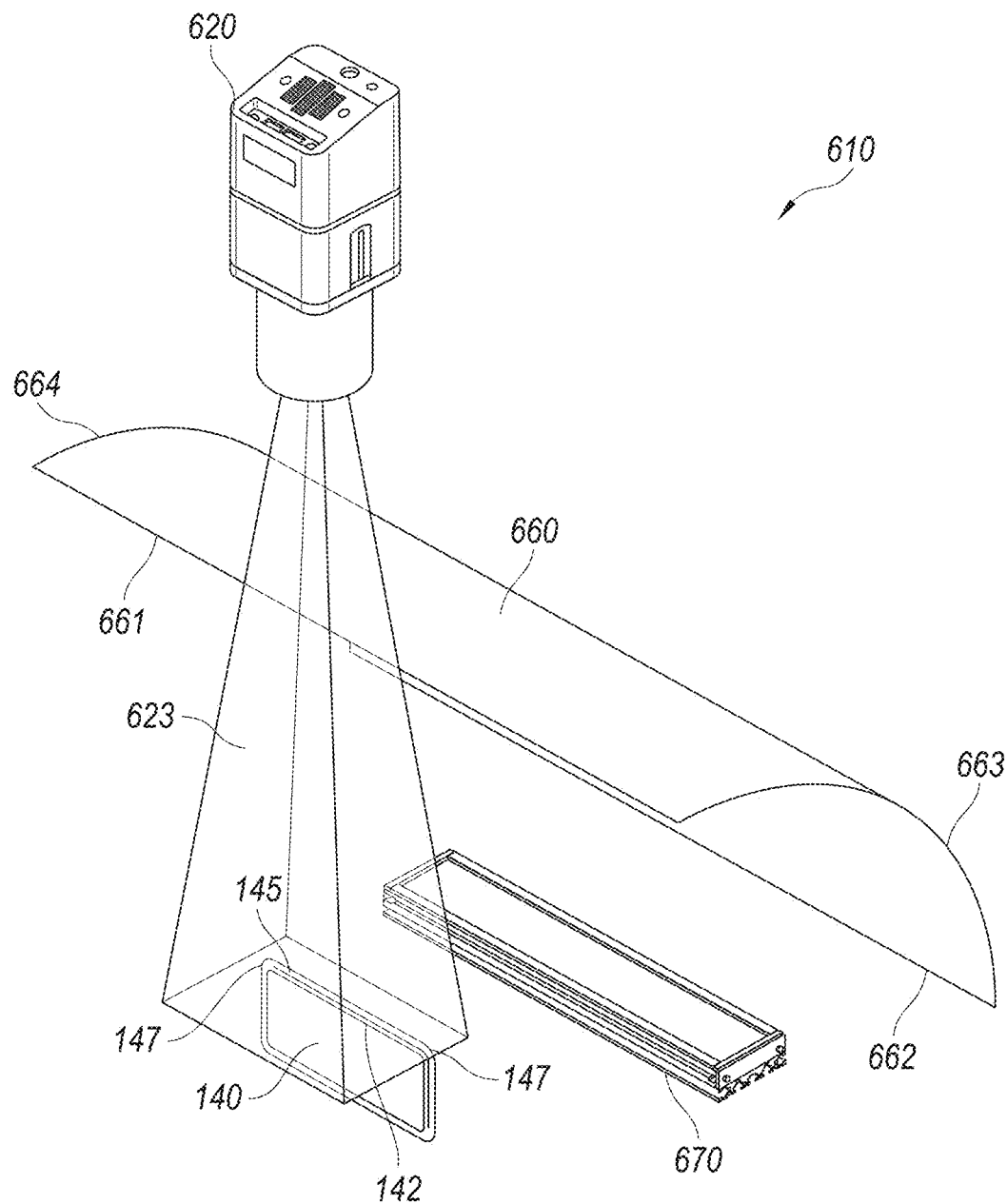
FIG. 6A is an isometric view and FIG. 6B is a side view of an adaptive diffuse illumination system configured in accordance with yet another embodiment of the present technology.
Figure 6B:
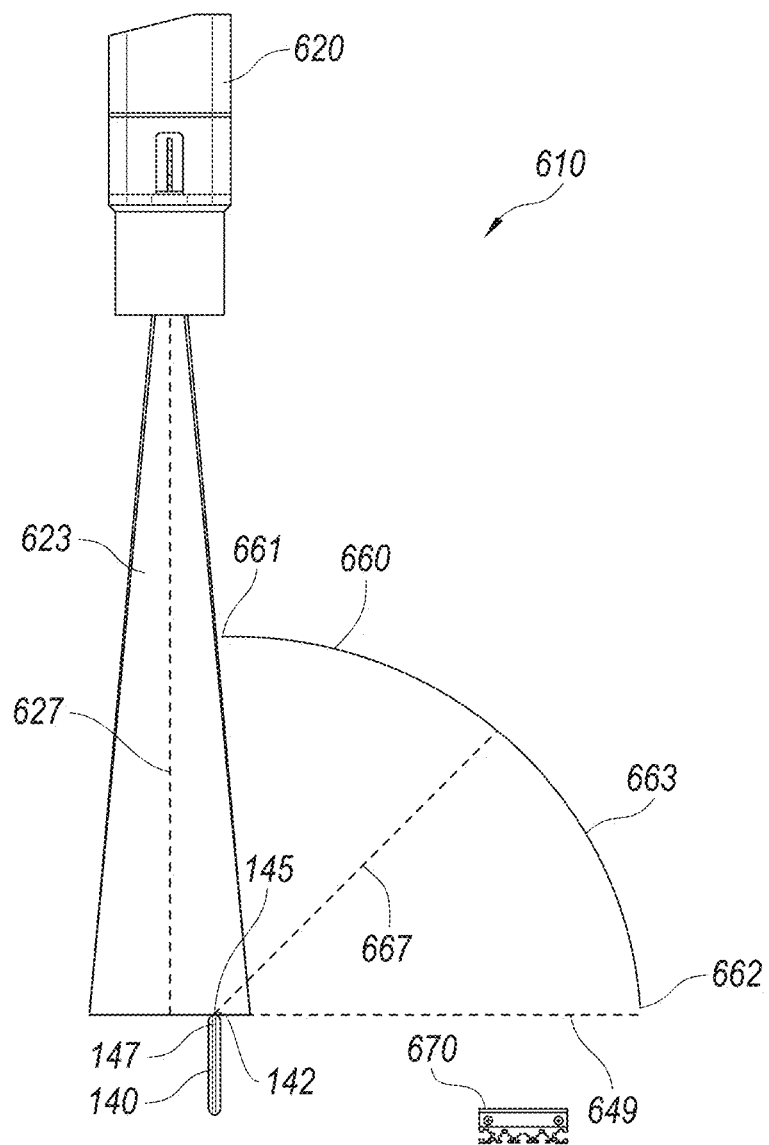

FIG. 6A is an isometric view and FIG. 6B is a side view of an adaptive diffuse illumination system 610 in accordance with another embodiment of the present technology. Similar to systems 110 and 210 (FIGS. 1 and 2), the system 610 includes a machine 620 having a field of view 623 ("FOV 623") (e.g., a field of view orthogonal to a curved surface 145 of an edge feature 142 of a UUT 140). However, the system 610 includes a diffuser arc 660 and a light source 670 (e.g., a light bar) in addition to, or in lieu of, the diffuser screen 150 and/or the light source 130 (FIGS. 1 and 2). Although not shown so as to avoid unnecessarily obscuring the description of this embodiment of the technology, the system 610 can also include other machines (e.g., machines 120 and/or 620) to inspect the same and/or one or more other features of the UUT 140 and may also include other hardware and/or components necessary for machine vision, including one or more processors, software, and/or output devices. For example, the system 610 can include signal processing hardware and/or software to analyze data captured by the machine 620, and/or a display for providing feedback (e.g., that a defect has been detected, that no defects were identified, that any identified defects are within a tolerance threshold, etc.) to a system user.

The system 610 is configured to visually inspect one or more features of a unit under test 140 ("UUT 140") for defects and/or other characteristics. In FIGS. 6A and 6B, the UUT 140 is a mobile device having an edge feature 142 with a curved surface 145. In other embodiments, however, the UUT 140 can be any other object and/or device that can be subjected to machine vision and/or inspection. For example, the UUT 140 in other embodiments can be any object and/or device that has a specular surface with a principle axis of curvature significantly longer than the subsequent radii of additional axes (e.g., an appliance part, a vehicle part and/or trim, durable good surfaces, an edge of a laptop cover, etc.). In some embodiments, the system 610 can include clamps and/or stands (not shown) to position and/or orient one or more features of the UUT 140 toward the machine 620. As illustrated in FIG. 6B, the UUT 140 is positioned within and slightly offset from the center (shown by dashed line 627) of the FOV 623 of the machine 620. In other embodiments, however, the UUT 140 can be positioned at other locations (e.g., at the center, at an edge, and/or at the opposite side of the dashed line 627) within the FOV 623 of the machine 620. Similar to systems 110 and 210 of FIGS. 1 and 2, the system 610 overcomes several challenges of uniformly illuminating one or more curved features of a UUT (e.g., curved surface 145 of edge feature 142 of UUT 140). Even so, the system 610 is not limited to uniformly illuminating curved feature (s) of a UUT, and a person skilled in the art will readily recognize that the system 610 can be used to illuminate (e.g., uniformly or otherwise) other features of a UUT having various shapes, contours, and/or characteristics.

The diffuser arc 660 of system 610 is an arc lined with diffuse material and sized according to the radius length of an inspected feature (e.g., of edge feature 142) of the UUT 140 and to the FOV 623 of the machine 620. More specifically, the diffuser arc 660 is sized according to the ray propagation of the illumination from the point of observation of the machine 120. In some embodiments, the diffuser arc 660 can include diffuser panels (not shown) at edges of the diffuser arc 660 (e.g., at edges 661, 662, 663, and/or 664) to extend the size and/or curvature of the arc and/or to extend an illumination profile of a UUT 140 around radiused corners 147 of the UUT 140.

Similar to the diffuser screen 150, the diffuser arc 660, in operation, is configured to lessen and/or remove harsh qualities (e.g., hotspots, saturated areas, and/or shadows) of an illumination profile of the UUT 140 that often result from direct specular illumination. In particular, the diffuser arc 660 of system 610 is configured to spread and/or disperse (e.g., reflect) specular illumination from the light source 670 into diffuse illumination and onto the curved surface 145 of the UUT 140. In this manner, the diffuser arc 660 increases the apparent beam size of the specular illumination (thereby minimizing and/or eliminating unwanted shadows in the illumination profile of the UUT 140) while also decreasing the illumination intensity of the specular illumination (thereby minimizing and/or eliminating hotspots and/or saturated areas). In turn, the diffuser arc 660 minimizes and/or eliminates the need for and/or importance of image processing intensity corrections.

Although shown separate from the light source 670 in the embodiment illustrated in FIGS. 6A and 6B, the diffuser arc 660 can incorporate and/or can be attached to the light source 670 in other embodiments. For example, in some embodiments, the light source 670 can be placed behind and/or attached to the diffuser arc 650 (e.g., such that the diffuser arc 660 is rear projected). In these and other embodiments, the diffuser arc 660 can be patterned to alter at least a portion of the specular illumination projected from the light source 670 and/or before the specular illumination reaches the UUT 140. For example, the diffuser arc 660 can be passive and can be manufactured with a specific pattern and/or can have a pattern subsequently applied (e.g., affixed) to it. In addition or alternatively, the diffuser arc 660 can be active, and can be programmed or otherwise configured to project and/or exhibit a specific pattern (e.g., before the UUT 140 is illuminated and/or in response to feedback regarding a previous and/or current illumination profile). In these and still other embodiments, the diffuser arc 660 (a) can include openings in the arc to permit at least a portion of the specular illumination from the light source 670 to pass through the diffuser arc 660 unhindered (e.g., to prevent reflection to the UUT 140), (b) can be a specific color, (c) can be configured to reflect one or more specific colors and/or intensities of illumination, and/or (4) can include one or more (e.g., polarization, color, and/or intensity) filters.

Referring to FIG. 6B, the first edge 661 of the diffuser arc 660 in system 610 is oriented parallel with the edge feature 142 of the UUT 140. More specifically, the diffuser arc 660 and/or the UUT 140 is positioned such that the first edge 661 of the diffuser arc 660 is just outside of the FOV 623 of the machine 620 while the second edge 662 of the diffuser arc 660 is positioned slightly above a horizontal plane 649 that is tangential to the center point of the curved surface 145 of the edge feature 142 of the UUT 140. Furthermore, the diffuser arc 660 and/or the UUT 140 is positioned at a location such that the center point of the curved surface 145 of the edge feature 142 is concentric with the diffuser arc 660 (as shown by dashed line 667). In other embodiments, the diffuser arc 660 and/or the UUT 140 can be positioned and/or oriented in different arrangements that shown in FIGS. 6A and 6B.

As discussed above, the light source 670 in the adaptive diffuse illumination system 610 is a light bar (e.g., of one or more colors). In other embodiments, however, the light source 670 can be any other light source described above with respect to FIG. 1. For example, the light source 670 can be a projector and can pattern, color, shape, and/or otherwise alter specular illumination projected onto the diffuser arc 660 in accordance with the discussion of FIGS. 5A-5C above (e.g., to further reduce the luminescence gradient across an illumination profile of the UUT 140).

As shown in FIG. 6B, the light source 670 is positioned (a) outside of the FOV 623 of the machine 620 and (b) below the diffuser arc 660 and the curved surface 145 of the UUT 140. In operation, the light source 670 is configured to project specular illumination onto the diffuser arc 660, which, in turn, is configured to reflect diffuse illumination toward the curved surface 145 of the edge feature 142 of the UUT 140. In other embodiments, the system 610 can include more than one light source (e.g., of the same or different types) and/or a light source at different positions and/or orientations.

Figure 7:
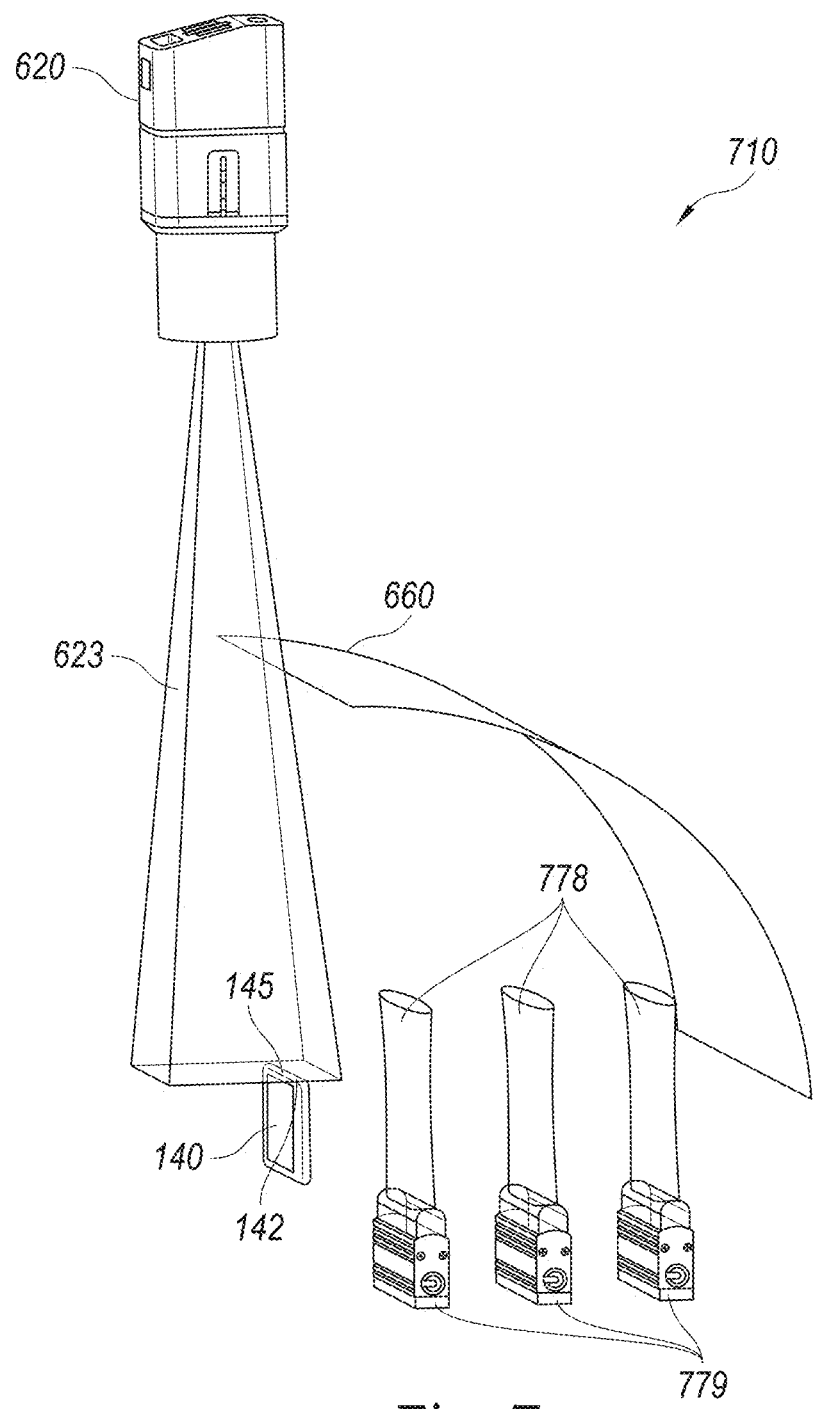
FIG. 7 is an isometric view of an adaptive diffuse illumination system configured in accordance with still another embodiment of the present technology.

For example, FIG. 7 illustrates a system 710 in accordance with another embodiment of the present technology. As shown, the system 710 includes multiple light sources 779 positioned at various distances from the UUT 140. The light sources 779 are configured to project focused, specular illumination 778 onto the diffuser arc 660. Each of the light sources 779 can be individually adjusted to project focused, specular illumination 778 at a desired intensity, pattern, and/or color (e.g., to shape and/or customize the illumination profile of the UUT 140). Although the system 710 is illustrated with three light sources 779, the system 710 can include a greater or lesser number of light sources in other embodiments. In these and other embodiments, the system 610 and/or the system 710 can include one or more light sources 670 and/or 779 positioned at various heights (e.g., in an array). In these and still other embodiments, the systems 610 and/or 710 can include light sources on the side and/or on the top of the diffuser arc 660 in addition to or in lieu of the light source(s) 670 and/or 779.

In operation, the systems 610 and 710 are configured to uniformly illuminate the curved surface 145 of the edge feature 142 of the UUT 140. During illumination, the machine 620 captures data (e.g., analog and/or digital images) of a portion (e.g., all or a subset) of the curved surface 145 within its FOV 623. Data captured by the machine 620 can then be passed to signal processing hardware and/or software to identify defects on the curved surface 145 of the edge feature 142 of the UUT 140. For example, data captured by the machine 120 can be analyzed to identify defects (e.g., cosmetic defects) and/or to distinguish defects from known components and/or desired characteristics of the curved surface 145 of the edge feature 142. Because the diffuser arc 660 minimizes and/or eliminates saturated areas from an illumination profile of an illuminated feature of the UUT, the system 610 and/or the system 710 minimize the need for and/or importance of imaging processing intensity corrections (e.g., of applying a gradient offset or image compensation to the data by subtracting gray level from non-uniform areas). Furthermore, the efficacy and/or efficiency of signal processing analysis and techniques are increased. In addition, these system orientations allow broad access to the UUT 140 and/or broad ranges of possible UUT positions and/or orientations. Moreover, these orientations allow manageable system size and permit the FOV 623 of the machine 620 to remain orthogonal to the curved surface 145 of the UUT 140. In addition, these system orientations permit on-axis illumination and data capture with little to no ghosting, attenuation, or gross keystone distortions that are noticeable in conventional machine vision illumination systems and techniques. Furthermore, most (if not all) of the specular illumination projected in the systems 610 and/or 710 is used to illuminate the feature of the UUT 140.

Figure 8A:
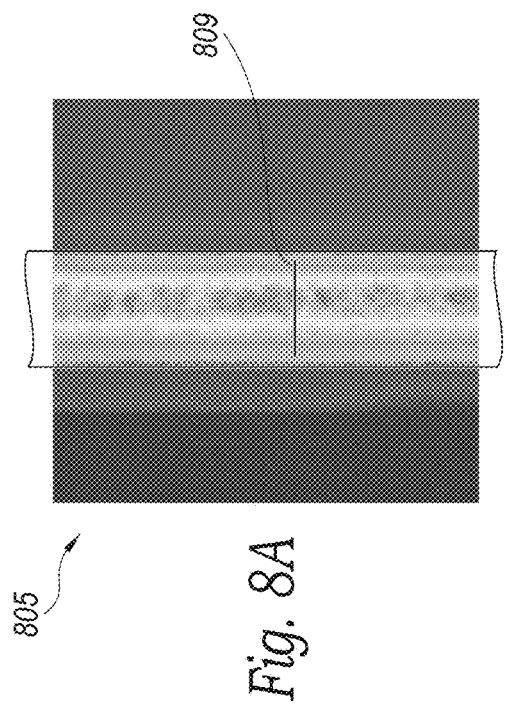
FIG. 8A is a luminescence heat map of an illumination profile of a curved surface of an edge feature of a unit under test using the adaptive diffuse illumination system of FIGS. 6A and 6B.
Figure 8B:
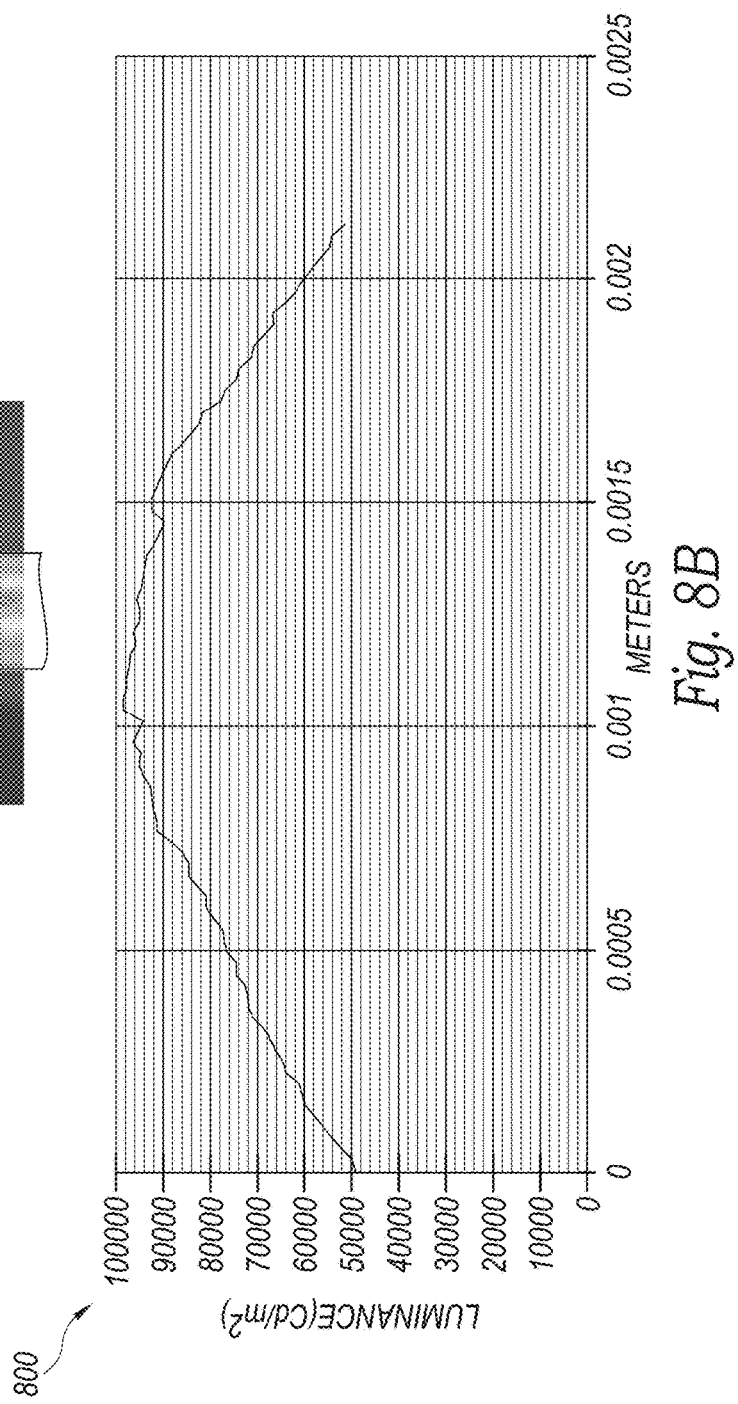
FIG. 8B is a line plot of luminescence measures along a portion of the illumination profile illustrated in FIG. 8A.

FIGS. 8A and 8B illustrate these advantages. FIG. 8A, for example, is a luminescence heat map 805 of an illumination profile of a curved surface of a UUT (e.g., the curved surface 145 of the edge feature 142 of the UUT 140) created using the adaptive diffuse illumination system 610 of FIGS. 6A and 6B. FIG. 8B is a line plot 800 of luminescence measures along a portion of the illumination profile illustrated in FIG. 8A. More specifically, the x-axis of the line plot 800 in FIG. 8B traces a portion 809 of the illumination profile illustrated in FIG. 8A. For purposes of illustration, the portion 809 was intentionally selected to trace the width of the curved surface of the UUT. The line plot 800 of FIG. 8B represents a true measure of luminescence along the portion 809. As shown, luminescence measures across the entirety of the portion 809 are well below the saturation value of the machine (e.g., approximately 2,500,000 $Cd/m^2$, as explained above). Thus, there is not a saturated region in the portion 809, meaning that the adaptive diffuse illumination system 610 can inspect the entire range of the portion 809. Furthermore, and as shown in FIG. 8A, the portion 809 is a representative portion of the majority of the illustrated illumination profile. This means that the system 610 can also inspect the entirety of the illustrated illumination profile of the curved surface of the UUT. Moreover, the gradient of illumination across the portion 809 is far less severe than the corresponding gradient of the portion 309 (illustrated in FIGS. 3A-C) created using a conventional brightfield illumination system. Therefore, the system 610 is able to more easily and/or efficiently identify defects (e.g., cosmetic defects) and/or distinguish defects from known components and/or desired characteristics of the UUT. This, in turn, (a) minimizes and/or eliminates the need for and/or importance of downstream imaging processing techniques and/or corrections, and/or (b) decreases the amount of time required to adequately and/or accurately inspect the curved surface of the UUT. Even with these improvements, however, the system 610 could benefit from additional adjustment of the illumination profile (e.g., by using a projector and/or light sources 779 of FIG. 7 to shape, pattern, color, and/or otherwise alter the specular illumination projected onto the diffuser arc 610 in accordance with the discussion of FIGS. 5A-5C and 7 above).

Figure 9A:
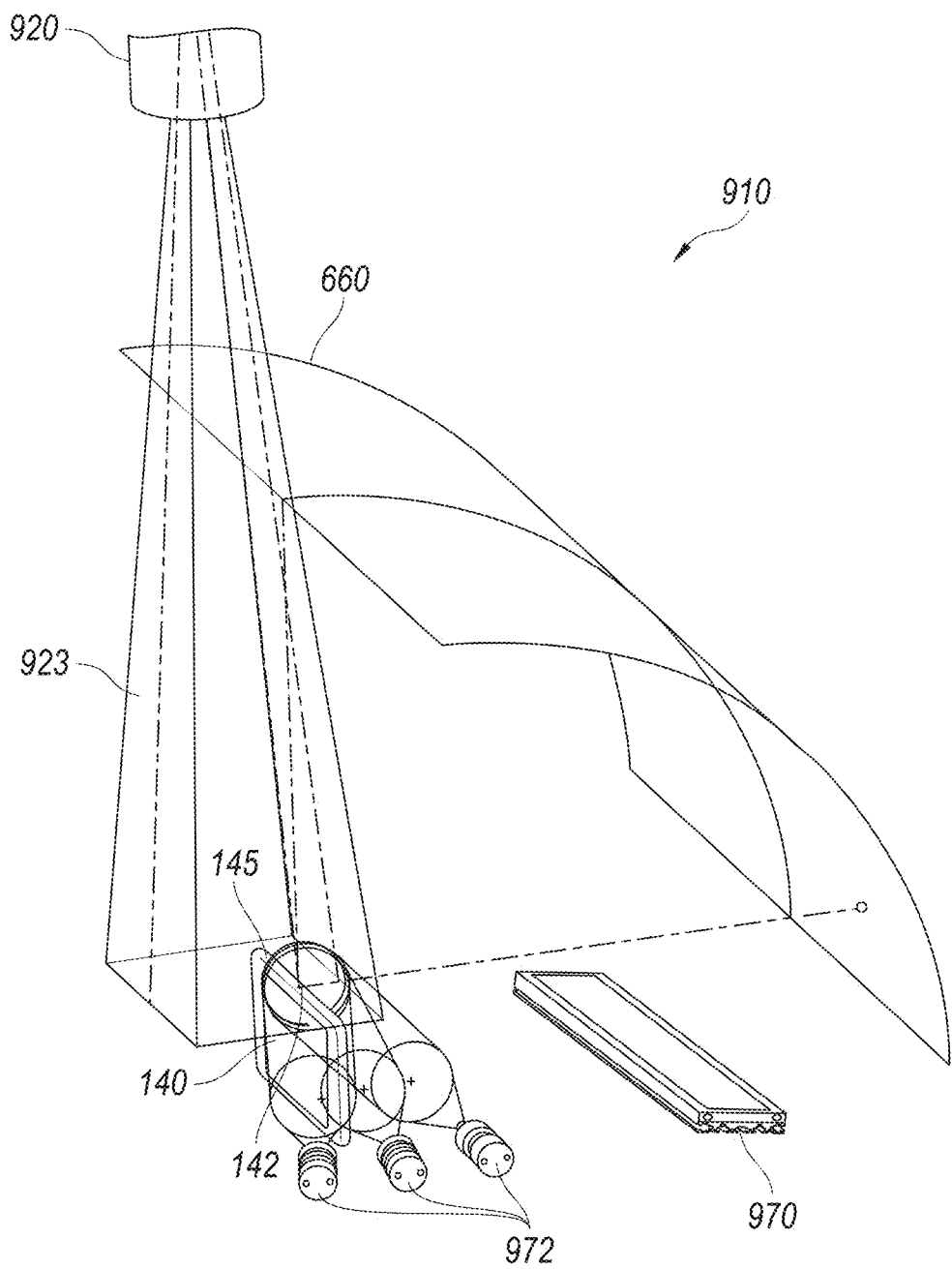
FIG. 9A is an isometric view of an adaptive diffuse illumination system configured in accordance with still another embodiment of the present technology.

FIG. 9A illustrates an adaptive diffuse illumination system 910 configured in accordance with still another embodiment of the present technology. As explained in greater detail below, the system 910 differs from the system 610 (FIGS. 6A and 6B) and/or the system 710 (FIG. 7) in that system 910 incorporates darkfield data capture techniques in addition to or in lieu of the brightfield data capture techniques explained above. As shown, the system 910 includes a diffuser arc 660 and a machine 920 (e.g., machine 620 or another machine capable of (1) darkfield data capture or (2) darkfield and brightfield data capture). The machine 920 has a field of view 923 (e.g., a field of view orthogonal to the curved surface 145 of the edge feature 142 of the UUT 140). Similar to system 610 and/or system 710 explained above, the system 910 can also include other machines (e.g., machines 120 and/or 620) (e.g., to inspect the same and/or one or more other features of the UUT 140) and/or can also include other hardware and/or components necessary for machine vision, including one or more processors, software, output devices, one or more brightfield light sources (e.g., one or more light sources 130, 670, and/or 779; FIGS. 1, 2, 6A, 6B, and/or 7), clamps, and/or stands (not shown so as to avoid unnecessarily obscuring the description of the embodiment of the technology).

As illustrated in FIG. 9A, the system 910 includes one or more collimated darkfield light sources 972 in addition to a brightfield light source 970 (e.g., light source 670 and/or light sources 779; FIGS. 6 and/or 7). In other embodiments, the system 910 can include one or more collimated darkfield light sources 972 in lieu of brightfield light source(s). In accordance with embodiments of the present technology, the collimated light source(s) 972 of the system 910 can be any source of illumination configured to project focused, specular illumination. For example, a collimated light source 972 can be a projector, a flashlight, a laser, a light source 779, and/or another type of light source. The light source 972 of FIG. 9A can also be configured to project various illumination intensities, patterns, shapes, and/or colors of specular illumination. FIG. 9A illustrates three possible positions and orientations of the collimated light source(s) 972 within the system 910. As explained below, a collimated light axis of the light source(s) 972 in these positions and orientations remains in a horizontal plane defined by an axis of the curved surface 145 of the UUT 140. Although the system 910 in FIG. 9A is illustrated with three possible collimated light source positions and orientations, a person skilled in the art will readily recognize that other positions and/or orientations are possible and fall within the scope of other embodiments of the present technology. For example, the system 910 can have a greater or lesser number of light sources 972 in a matching number of positions and/or orientations about the UUT 140.

Figure 9B:
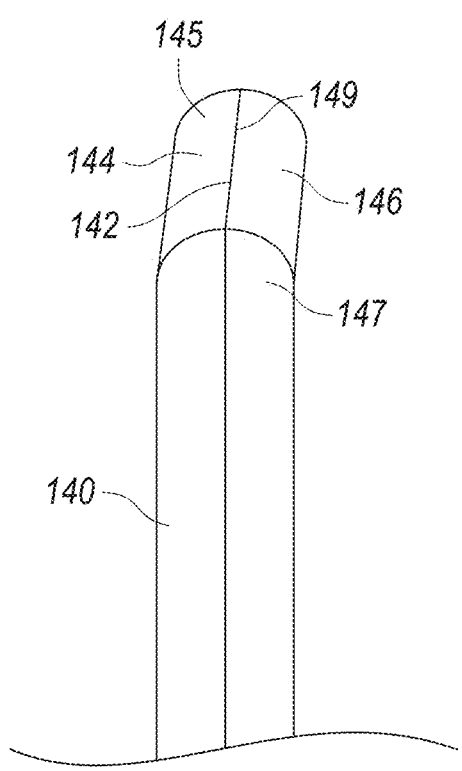
FIG. 9B is an orthogonal view.

FIG. 9B illustrates the UUT 140 of FIG. 9A. As shown, the UUT 140 includes an edge feature 142 having a curved surface 145 similar to the UUTs 140 described above with respect to FIGS. 1-8B. Also illustrated, however, is a center point axis 149 that divides the curved surface 145 into a front side 144 and a back side 146.

In operation, the system 910 is able to create and/or adjust a darkfield illumination profile of one or more features of the UUT 140 (e.g., of the curved surface 145 of the edge feature 142). Referring to FIGS. 9A and 9B together, the collimated light source(s) 972 is (are) positioned and/or oriented such that a collimated light axis of the light source(s) 972 remains in a horizontal plane defined by an axis (e.g., the center point axis 149) running along the curved surface 145 of the UUT. The collimated light source(s) 972 is (are) configured to project focused, specular illumination across and along at least a portion of the curved surface 145 (e.g., along the center point axis 149) of the UUT 140 such that the machine 920 does not view the focused, specular illumination in the absence of a defect (e.g., a cosmetic defect) on the portion of the curved surface 145. As explained below, this orientation prevents crosstalk between the darkfield illumination and any brightfield illumination present.

Figure 9C:
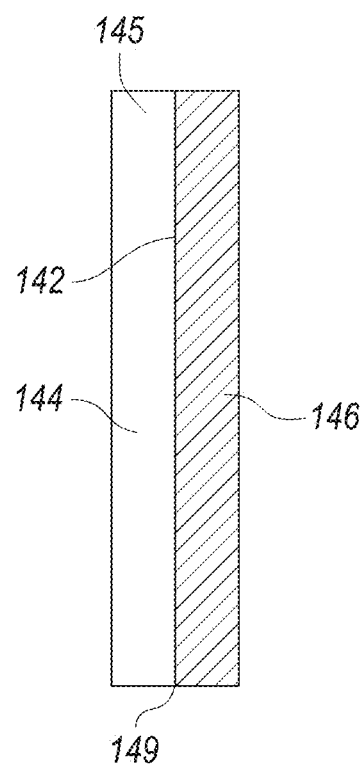
FIGS. 9C and 9D are top views, of a curved surface of an edge feature of units under test illuminated using the adaptive diffuse illumination system of FIG. 9A.
Figure 9D:
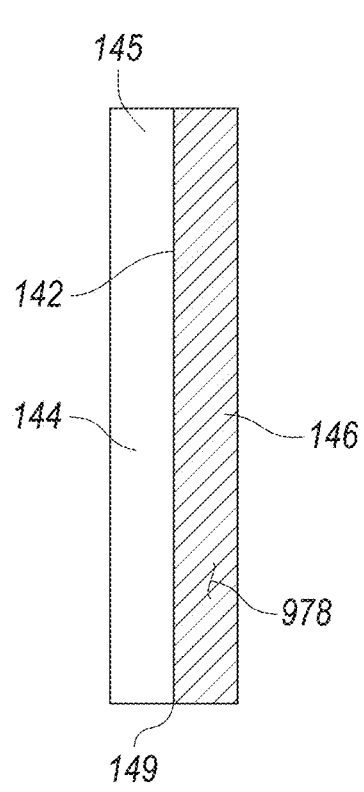

FIGS. 9C and 9D are top views of the curved surface 145 of the UUT 140 from the perspective of the machine 920 of the system 910. In accordance with this embodiment, the system 910 uses brightfield illumination techniques (e.g., the brightfield illumination techniques described above with respect to FIGS. 1-8B) to illuminate at least a portion (e.g., all or a subset of) the front side 144 of the curved surface 145 and uses a darkfield illumination technique to illuminate at least a portion (e.g., all or a subset of) the back side 146 of the curved surface 145. In FIGS. 9C and 9D, the system 910 illuminates all of the front side 144 of the UUT 140 using the brightfield technique described above with respect to FIGS. 6A and 6B and illuminates all of the back side 146 of the UUT 140 using the darkfield technique described above with respect to FIGS. 9A and 9B. The positioning and orientation of the light source(s) 972 (as described above) ensure that darkfield illumination on the back side 146 of the curved surface 145 does not crosstalk with brightfield illumination on the front side 144 of the curved surface 145. In other words, the positioning and orientation of the light source(s) 972 permit the illumination types to meet but not cross over the center point axis 149 of the UUT 140 or another desired boundary.

As shown in FIGS. 9C and 9D, the machine 920 views the entirety of the front side 144 of the UUT 140 as illuminated by the brightfield illumination, and the front side 144 is analyzed (e.g., inspected) according to brightfield inspection techniques (e.g., the brightfield inspection techniques described above). In contrast, the machine 920 does not view any portion of the back side 146 of the UUT 140 in FIG. 9C as illuminated by the darkfield illumination. This is because the back side 146 of the UUT 140 in FIG. 9C is devoid of any defects (e.g., cosmetic defects). In FIG. 9D, however, the machine views a portion 978 of the back side 146 of the UUT 140 as illuminated. This is because the back side 146 has a defect located at the portion 978 that has reflected darkfield illumination toward the machine 920. In this manner, the system 910 is able to inspect portions of the UUT 140 that are not illuminated by brightfield illumination, which permits the system 910 to perform multiple inspection processes on a single captured image. Thus, the time required to adequately and/or accurately inspect one or more features of the UUT is decreased.

FIG. 9E is a luminescence heat map 905 of an illumination profile of a curved surface of an edge feature of a UUT (e.g., the curved surface 145 of the edge feature 142 of the UUT 140; FIGS. 1, 2, 6A, 6B, 7, and/or 9A-9D) created using the adaptive diffuse illumination system 910 with a collimated darkfield light source 972 in the rightmost position illustrated in FIG. 9A. FIG. 9F is a line plot 900 of luminescence measures along a portion of the illumination profile illustrated in FIG. 9E. More specifically, the x-axis of the line plot 900 in FIG. 9F traces a portion 909 of the illumination profile illustrated in FIG. 9E. For purposes of illustration, the portion 909 was intentionally selected to trace the width of the curved surface of the UUT and to intersect with a defect 978 in the curved surface of the edge feature of the UUT. As shown in FIGS. 9E and 9F, the center point axis 149 of the curved surface 145 is present at about 0.00225 meters, which divides the curved surface 145 into a front side 144 illuminated using brightfield illumination (e.g., from 0.0 meters to about 0.00225 meters in the line plot 900) and a back side 146 illuminated using darkfield illumination (e.g., from about 0.00225 meters to about 0.00425 meters in the line plot 900).

The line plot 900 of FIG. 9F represents a true measure of luminescence along the portion 909. As shown, luminescence measures across the entirety of the portion 909 are well below the saturation value of the machine 920 (e.g., approximately 2,500,000 Cd/m$^2$, as explained above). Thus, there is not a saturated region in the portion 909, meaning that the adaptive diffuse illumination system 910 can inspect the entire range of the portion 909. Furthermore, and as shown in FIG. 9E, the portion 909 is a representative portion of the majority of the illustrated illumination profile. This means that the system 910 can also inspect the entirety of the illustrated illumination profile of the curved surface of the UUT, including a portion (e.g., all or a subset) of the front side 144 of the curved surface of the UUT using brightfield illumination techniques (e.g., the brightfield illumination techniques described above). In addition, the gradient of illumination across the portion 909 is less severe than the corresponding gradient across the portion 309 (illustrated in FIGS. 3A-C) created using a conventional brightfield illumination system. Therefore, the system 910 is able to more easily and/or efficiently identify defects (e.g., cosmetic defects) and/or distinguish defects from known components (e.g., known component 907) and/or desired characteristics of the UUT. This, in turn, (a) minimizes and/or eliminates the need for and/or importance of downstream imaging processing techniques and/or corrections, and/or (b) decreases the amount of time required to adequately and/or accurately inspect the curved surface of the UUT.

Separately and/or at the same time, the adaptive diffuse illumination system 910 can inspect a portion (e.g., all or a subset) of the UUT that is illuminated with darkfield illumination instead of brightfield illumination. In FIGS. 9E and 9F, the back side 146 of the curved surface represents such a portion. As shown in FIG. 9F, the luminescence measures from the perspective of the machine 920 and across the back side 146 of the curved surface (e.g., represented by the portion 909 starting at about 0.0025 meters) are extremely low (e.g., around 25,000 CD/m$^2$ or less) with the exception of from about 0.0035 meters to about 0.00375 meters across the portion 909. Furthermore, there is very little gradient in luminescence across the back side 146 of the curved surface outside of this exception area. As shown in FIGS. 9E and 9F, this exception area corresponds to the location of the defect 978 in the portion 909 and is readily apparent in the line plot 900. In this manner, the system 910 is able to analyze the line plot 900 to easily and/or efficiently identify defects (e.g., cosmetic defects) and/or distinguish defects from known components (e.g., the known component 907) and/or desired characteristics of the UUT using darkfield inspection techniques on portions of the UUT 140 that are not currently and/or cannot be inspected with brightfield inspection techniques. Thus, system 910 (1) provides greater flexibility for use over systems that incorporate brightfield illumination and/or inspection alone, and/or (2) decreases the amount of time required to adequately and/or accurately inspect the curved surface of the UUT.

Figure 10:
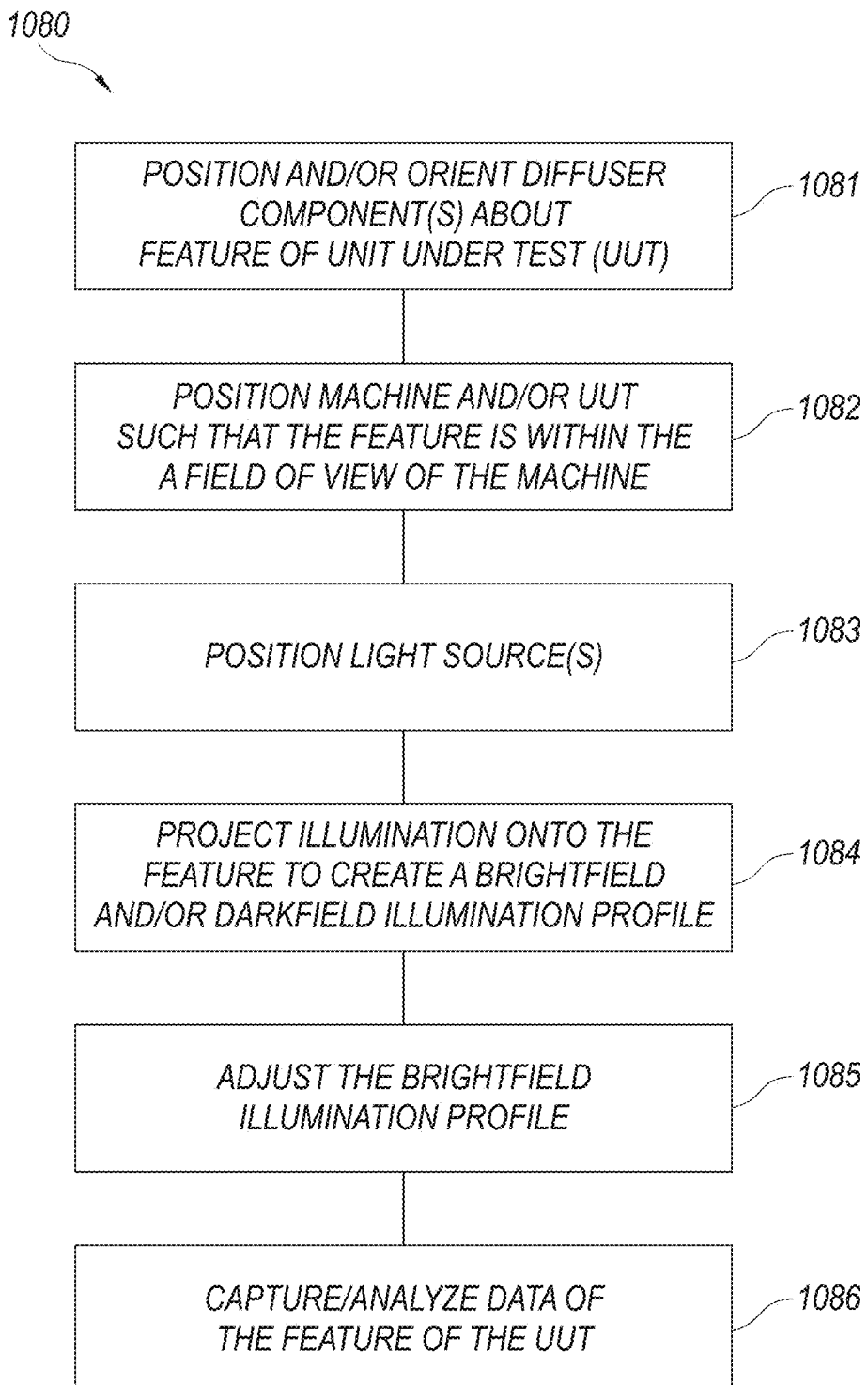
FIG. 10 is a flow diagram of a method or process in accordance with an embodiment of the present technology.

FIG. 10 is a flow diagram of a method or process 1080 for operating an adaptive diffuse illumination system (e.g., systems 110, 210, 610, 710, and/or 910; FIGS. 1, 2, 6A, 6B, 7 and/or 9A) in accordance with an embodiment of the present technology. As illustrated in FIG. 10, the method 1080 can begin at block 1081 by positioning and/or orienting one or more diffuser components of the system about one or more features of a unit under test (UUT). For example, the method 1080 can position and/or orient one or more diffuser screens (e.g., diffuser screen(s) 150; FIGS. 1 and 2) about one or more features (e.g., one or more curved surfaces 145 of one or more edge features 142) of a UUT (e.g., UUT 140) in any position and/or at any angle described above with respect to FIGS. 1-5C. Additionally or alternatively, the method 1080 can position and/or orient one or more diffuser arcs (e.g., diffuser arc(s) 660; FIGS. 6A, 6B, 7, and 9A) about the feature(s) of the UUT in accordance with the discussion above with respect to FIGS. 6A-9F. In these and other embodiments, the diffuser component(s) can be stationary and/or at fixed position(s) and/or orientation(s), and the method 1080 can position and/or orient the UUT about the diffuser component(s).

At block 1082, the method 1080 can position a machine and/or the UUT such that the feature(s) of the UUT is (are) within a field of view of the machine. For example, the method 1080 can position the machine (e.g., machine 120, 620, and/or 920; FIGS. 1, 2, 6A, 6B, 7, and/or 9A) such that its field of view contains and is orthogonal to the feature(s) of the UUT. In other embodiments, the method 1080 can position the machine such that its field of view contains but is not orthogonal to the feature of the UUT. Additionally or alternatively, the method 1080 can position the UUT to place and/or orient the feature of the UUT at a desired location and/or orientation within the field of view of the machine (e.g., using a stand and/or a clamp of the system). In these and still other embodiments, the method 1080 can position multiple machines (e.g., to inspect the same and/or one or more other features of the UUT).

At block 1083, the method 1080 can position one or more light sources about the feature(s) of the UUT. For example, the method 1080 can position one or more light sources (e.g., light sources 130, 670, 779, and/or 972; FIGS. 1, 2, 6A, 6B, 7, and/or 9A) at various heights, distances, positions, and/or orientations about the feature(s) of the UUT in accordance with the discussion above with respect to FIGS. 1-9F. In other embodiments, the light source(s) can be stationary and/or at fixed position(s) and/or orientation(s), and the method 1080 can position (e.g., reposition or otherwise) and/or orient (e.g., reorient or otherwise) the UUT. At block 1084, the method 1080 can project illumination onto the feature(s) of the UUT to create one or more brightfield illumination profiles and/or one or more darkfield illumination profiles. For example, in some embodiments, the method 1080 can project specular illumination (e.g., from the light source(s)) onto the diffuser component(s) of the system and/or onto the feature(s) of the UUT. In these and other embodiments, the method 1080 can reflect, spread, disperse, and/or otherwise manipulate the specular diffusion to create and/or direct (e.g., reflect, redirect, and/or focus)

diffuse and/or specular illumination onto the feature(s) of the UUT. In these and still other embodiments, the method 1080 can shape, color, pattern, filter, and/or otherwise alter (e.g., change the intensity of) the specular illumination and/or the diffuse illumination before and/or while it is projected onto the diffuser component(s) and/or onto the feature(s) of the UUT (e.g., using one or more active and/or passive diffuser components and/or one or more active and/or passive light sources).

At block 1085, the method 1080 can adjust the brightfield illumination profile(s) of the feature(s) of the UUT. For example, the method 1080 can shape, color, pattern, filter, and/or otherwise alter (e.g., change the intensity of) a portion (e.g., all or a subset) of the illumination (e.g., specular and/or diffuse) projected onto the diffuser component(s) and/or onto the feature(s) of the UUT by adjusting the light source and/or the diffuser component. In some of these embodiments, the method 1080 can adjust the light source and/or the diffuser component in response to feedback received, for example, from the machine, signal processing hardware and/or software, and/or other components of the system. In this manner, the method 1080 can create and/or adjust (e.g., customize) the illumination profile(s) (e.g., while the feature(s) of the UUT are exposed to the machine). In other embodiments, the method 1080 can reposition and/or reorient the UUT, one or more diffuser components, and/or one or more light sources of the system. In these and still other embodiments, the method 1080 can add additional diffuser component(s) and/or light source(s) to the system, and/or the method 1080 can alter existing light sources and/or diffuser component(s) (e.g., by manipulating one or more diffuser panels) of the system.

At block 1086, the method 1080 can capture and/or analyze data of the feature(s) of the UUT. For example, the method 1080 can capture one or more images (e.g., one or more digital and/or analog images) of the feature(s) of the UUT using the machine(s). The method 1080 can pass these images to signal processing hardware and/or software of the system and/or another system to analyze (e.g., inspect all or a subset of) the feature(s) of the UUT (e.g., using brightfield and/or darkfield inspection techniques as appropriate). The method 1080 can also proceed beyond block 1086, for example, to make one or more decisions based on the results of the analysis. For example, the method 1080 can determine that one or more features of the UUT pass and/or do not pass quality control and/or other threshold limits (e.g., standards). In these and other embodiments, the method 1080 can pass and/or display the results of the analysis to a user of the system and/or to another system (e.g., another machine vision and/or analysis system).

Although the steps of method 1080 are discussed and illustrated in a particular order, the method 1080 is not so limited. In other embodiments, the method 1080 can perform steps in a different order. For example, the method 1080 can capture and/or analyze data of the feature(s) of the UUT before, during, and/or after the method 1080 performs steps 1084 and/or 1085. Furthermore, a person skilled in the art will readily recognize that the method 1080 can be altered and still remain within these and other embodiments of the present technology. For example, one or more steps illustrated in FIG. 10 can be omitted from and/or repeated within method 1080 in some embodiments.

Although not shown so as to avoid unnecessarily obscuring the description of the embodiments of the technology, any of the foregoing systems and methods described above in FIGS. 1-10 can include and/or be performed by a computing device configured to direct and/or arrange components of the systems and/or to receive, arrange, store, analyze, and/or otherwise process data received, for example, from the machine and/or other components of the systems. As such, such a computing device includes the necessary hardware and corresponding computer-executable instructions to perform these tasks. More specifically, a computing device configured in accordance with an embodiment of the present technology can include a processor, a storage device, input/output device, one or more sensors, and/or any other suitable subsystems and/or components (e.g., displays, speakers, communication modules, etc.). The storage device can include a set of circuits or a network of storage components configured to retain information and provide access to the retained information. For example, the storage device can include volatile and/or non-volatile memory. As a more specific example, the storage device can include random access memory (RAM), magnetic disks or tapes, and/or flash memory.

The computing device can also include computer-readable media (e.g., the storage device, disk drives, and/or other storage media, excluding only a transitory, propagating signal per se) including computer-executable instructions stored thereon that, when executed by the processor and/or computing device, cause the systems to illuminate and/or analyze one or more features of a UUT as described in detail above with reference to FIGS. 1-10. Moreover, the processor can be configured for performing or otherwise controlling steps, calculations, analysis, and any other functions associated with the methods described herein.

In some embodiments, the storage device can store one or more databases used to store data collected by the systems as well as data used to direct and/or adjust components of the systems. In one embodiment, for example, a database is an HTML file designed by the assignee of the present disclosure. In other embodiments, however, data is stored in other types of databases or data files.

One of ordinary skill in the art will understand that various components of the systems (e.g., the computing device) can be further divided into subcomponents, or that various components and functions of the systems may be combined and integrated. In addition, these components can communicate via wired and/or wireless communication, as well as by information contained in the storage media.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. Furthermore, the various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A system for producing a uniform illumination pattern on a curved surface of a unit under test (UUT) for machine vision, the system comprising:
   a machine having a field of view directed toward the curved surface of the UUT;
   one or more light sources positioned outside of the field of view; and
   a diffuser element oriented about the curved surface of the UUT,
      wherein the diffuser element is positioned outside of the field of view, and
      wherein the one or more light sources are configured to project light onto the curved surface via the diffuser element to create an illumination profile on the UUT.

2. The system of claim 1 wherein the field of view of the machine is orthogonal to a plane tangential to a principal axis of curvature of the curved surface of the UUT, and wherein the principal axis of curvature is centered on the curved surface.

3. The system of claim 1 wherein the one or more light sources includes a projector.

4. The system of claim 3 wherein the projector is configured to define, at least in part, the illumination profile by shaping, coloring, patterning, and/or changing intensity of the light incident upon the curved surface via the diffuser element.

5. The system of claim 1 wherein the one or more light sources includes a light bar, a light bulb, a lamp, a flashlight, a laser, a light emitting diode, an array of light emitting diodes, and/or a flat panel display.

6. The system of claim 1 wherein the diffuser element is a flat projection screen.

7. The system of claim 1 wherein the diffuser element is a diffuser arc.

8. The system of claim 7 wherein the diffuser arc includes diffuser panels at ends of the diffuser arc that are configured to extend the illumination profile around radiused corners of the UUT.

9. The system of claim 1, wherein a dimension of the diffuser element is defined as a function of a radius length of the curved surface and of the field of view of the machine.

10. The system of claim 1 wherein the diffuser element is configured to:
    direct light from the one or more light sources to the curved surface of the UUT by (i) passing the light through the diffuser element and/or (ii) reflecting the light toward the curved surface of the UUT; and
    define, at least in part, the illumination profile by shaping, coloring, patterning, and/or changing the intensity of light incident upon the curved surface via the diffuser element.

11. The system of claim 1 wherein:
    the one or more light sources includes at least a first light source and a second light source;
    the first light source is positioned a first distance from the UUT and is configured to project a first portion of the light having a first intensity, a first pattern, and/or a first color; and
    the second light source is positioned a second distance from the UUT greater than the first distance and is configured to project a second portion of the light having a second intensity, a second pattern, and/or a second color.

12. The system of claim 1 wherein:
    the light is a first light;
    the one or more light sources are brightfield light sources;
    the one or more brightfield light sources are configured to project the first light onto a first portion of the curved surface;
    the system further includes one or more collimated, darkfield light sources; and
    the one or more collimated, darkfield light sources are configured to project a second light onto a second portion of the curved surface and along a horizontal plane defined by an axis of the curved surface.

13. A method of uniformly illuminating a curved surface of a unit under test (UUT) for machine vision, the method comprising:
    orienting a diffuser element about the curved surface of the UUT and outside a field of view of a machine that is directed toward the curved surface, wherein a dimension of the diffuser element is defined as a function of a radius length of the curved surface and the field of view;
    orienting one or more light sources to project illumination toward the diffuser element;
    projecting specular illumination onto the diffuser element using the one or more light sources; and
    directing diffuse illumination onto a first portion of the curved surface to create an illumination profile by transmitting and/or reflecting the specular illumination using the diffuser element.

14. The method of claim 13, further comprising shaping, coloring, and/or patterning at least a portion of the specular illumination using the one or more light sources and/or the diffuser element.

15. The method of claim 13, further comprising adjusting the illumination profile by shaping, coloring, patterning, filtering, and/or changing intensity of at least a portion of the specular illumination using the one or more light sources and/or the diffuser element.

16. The method of claim 15 wherein adjusting the illumination profile includes adjusting the illumination profile in response to feedback from the machine, signal processing hardware, and/or signal processing software.

17. The method of claim 15 wherein adjusting the illumination profile includes adjusting the illumination profile using the one or more light sources and/or the diffuser element while the curved surface is exposed to the machine.

18. The method of claim 13 wherein the one or more light sources are brightfield light sources, and wherein the method further comprises projecting darkfield illumination along a second portion of the curved surface using one or more darkfield light sources.

19. The method of claim 13, further comprising:
capturing images of the illumination profile using the machine; and
analyzing the captured images for cosmetic defects on the curved surface of the UUT.

20. The method of claim 13, further comprising positioning the curved surface of the UUT within the field of view of the machine such that the field of view of the machine is orthogonal to a plane tangential to a principal axis of curvature of the curved surface, wherein the principal axis of curvature is centered on the curved surface.

* * * * *

UNITED STATES PATENT AND TRADEMARK OFFICE
CERTIFICATE OF CORRECTION

PATENT NO. : 10,527,557 B2  
APPLICATION NO. : 16/208028  
DATED : January 7, 2020  
INVENTOR(S) : Mark Michniewicz et al.

Page 1 of 1

It is certified that error appears in the above-identified patent and that said Letters Patent is hereby corrected as shown below:

In the Drawings

On sheet 15 of 15, in Figure 10, reference numeral 1082, Lines 2-3, delete "THE A" and insert -- THE --, therefor.

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*